United States Patent
Tran et al.

(10) Patent No.: US 10,998,101 B1
(45) Date of Patent: May 4, 2021

(54) HEALTH MANAGEMENT

(71) Applicants: Bao Tran, Saratoga, CA (US); Ha Tran, Saratoga, CA (US)

(72) Inventors: Bao Tran, Saratoga, CA (US); Ha Tran, Saratoga, CA (US)

(*) Notice: Subject to any disclaimer, the term of this patent is extended or adjusted under 35 U.S.C. 154(b) by 0 days.

(21) Appl. No.: 16/714,759

(22) Filed: Dec. 15, 2019

(51) Int. Cl.
| | |
|---|---|
| *G16H 40/67* | (2018.01) |
| *G16H 20/30* | (2018.01) |
| *G06Q 50/00* | (2012.01) |
| *G16H 20/60* | (2018.01) |
| *G16H 10/60* | (2018.01) |
| *G06N 3/08* | (2006.01) |
| *G06N 3/04* | (2006.01) |
| *A61B 5/00* | (2006.01) |
| *A61B 5/145* | (2006.01) |
| *A61B 5/11* | (2006.01) |
| *A61B 5/0205* | (2006.01) |
| *G16H 50/30* | (2018.01) |
| *A61B 5/021* | (2006.01) |
| *G16H 50/50* | (2018.01) |
| *A61B 5/0537* | (2021.01) |

(52) U.S. Cl.
CPC .......... *G16H 40/67* (2018.01); *A61B 5/0205* (2013.01); *A61B 5/1118* (2013.01); *A61B 5/14532* (2013.01); *A61B 5/486* (2013.01); *A61B 5/4836* (2013.01); *A61B 5/4866* (2013.01); *A61B 5/7267* (2013.01); *A61B 5/7275* (2013.01); *G06N 3/04* (2013.01); *G06N 3/08* (2013.01); *G06Q 50/01* (2013.01); *G16H 10/60* (2018.01); *G16H 20/30* (2018.01); *G16H 20/60* (2018.01); *G16H 50/30* (2018.01); *G16H 50/50* (2018.01); *A61B 5/021* (2013.01); *A61B 5/0537* (2013.01)

(58) Field of Classification Search
CPC ........ G16H 40/67; G16H 50/30; G16H 50/50; G16H 20/60; G16H 20/30; G16H 10/60; A61B 5/7275; A61B 5/486; A61B 5/0537; A61B 5/021; A61B 5/7267; A61B 5/1118; A61B 5/4836; A61B 5/0205; A61B 5/14532; G06Q 50/01; G06N 3/08; G06N 3/04
See application file for complete search history.

(56) References Cited

U.S. PATENT DOCUMENTS

| | | |
|---|---|---|
| 4,014,321 A | 3/1977 | March |
| 6,043,492 A | 3/2000 | Lee |
| 8,747,336 B2 | 6/2014 | Tran |

(Continued)

OTHER PUBLICATIONS

Atkinson, F. S., Foster-Powell, K., & Brand-Miller, J. C. (2008). International tables of glycemic index and glycemic load values: 2008. Diabetes care, 31(12), 2281-2283. doi:10.2337/dc08-1239.

(Continued)

*Primary Examiner* — William J Levicky
*Assistant Examiner* — Alexander M Eisenberg
(74) *Attorney, Agent, or Firm* — Tran & Associates

(57) ABSTRACT

A method includes capturing continuously vital signs and motion data from one or more sensors adapted to be coupled to a user; capturing food consumption of the user; predicting a predetermined health condition of the user based on the vital signs; generating a plan for the predetermined health condition; and prompting the user to execute the plan with a closed-loop feedback based on sensor data.

20 Claims, 10 Drawing Sheets

(56) References Cited

U.S. PATENT DOCUMENTS

| | | |
|---|---|---|
| 9,445,759 B1 | 9/2016 | Lamego |
| 9,699,859 B1 | 7/2017 | Li |
| 9,820,658 B2 | 11/2017 | Tran |
| 10,154,460 B1* | 12/2018 | Miller ................ A61B 5/14546 |
| 10,252,058 B1* | 4/2019 | Fuerst .................... G16H 10/20 |
| 10,350,454 B1 | 7/2019 | Li |
| 2009/0177068 A1* | 7/2009 | Stivoric ............... A61B 5/7275 |
| | | 600/365 |
| 2010/0168537 A1 | 7/2010 | Ueda |
| 2010/0280838 A1 | 11/2010 | Bosworth |
| 2010/0295686 A1* | 11/2010 | Sloan ................ G08B 21/0453 |
| | | 340/573.1 |
| 2013/0178335 A1 | 7/2013 | Lin |
| 2016/0058133 A1* | 3/2016 | Fournier ................ A61B 5/091 |
| | | 455/41.2 |
| 2016/0086500 A1* | 3/2016 | Kaleal, III ............. G06T 19/00 |
| | | 434/257 |
| 2016/0106363 A1* | 4/2016 | O'Connell ............. G16H 40/63 |
| | | 600/301 |
| 2017/0128007 A1* | 5/2017 | Hayter ................ G09B 19/0092 |
| 2017/0344726 A1* | 11/2017 | Duffy ..................... G06Q 50/22 |
| 2017/0347894 A1* | 12/2017 | Bhushan ................ A61B 5/681 |
| 2018/0035930 A1 | 2/2018 | Sokolov |
| 2018/0074069 A1* | 3/2018 | Sokolov ............ A61B 5/14532 |
| 2019/0042896 A1* | 2/2019 | Sabripour .......... G06K 9/00791 |
| 2019/0180855 A1 | 6/2019 | Sysko |
| 2019/0385711 A1* | 12/2019 | Shriberg ................ G16H 10/20 |

OTHER PUBLICATIONS

Jennie Brand-Miller et al., "Moreover, Glycemic index, postprandial glycemia, and the shape of the curve in healthy subjects: analysis of a database of more than 1000 foods", Am J Clin Nutr 2009;89:97-105.

* cited by examiner

FIG. 2A

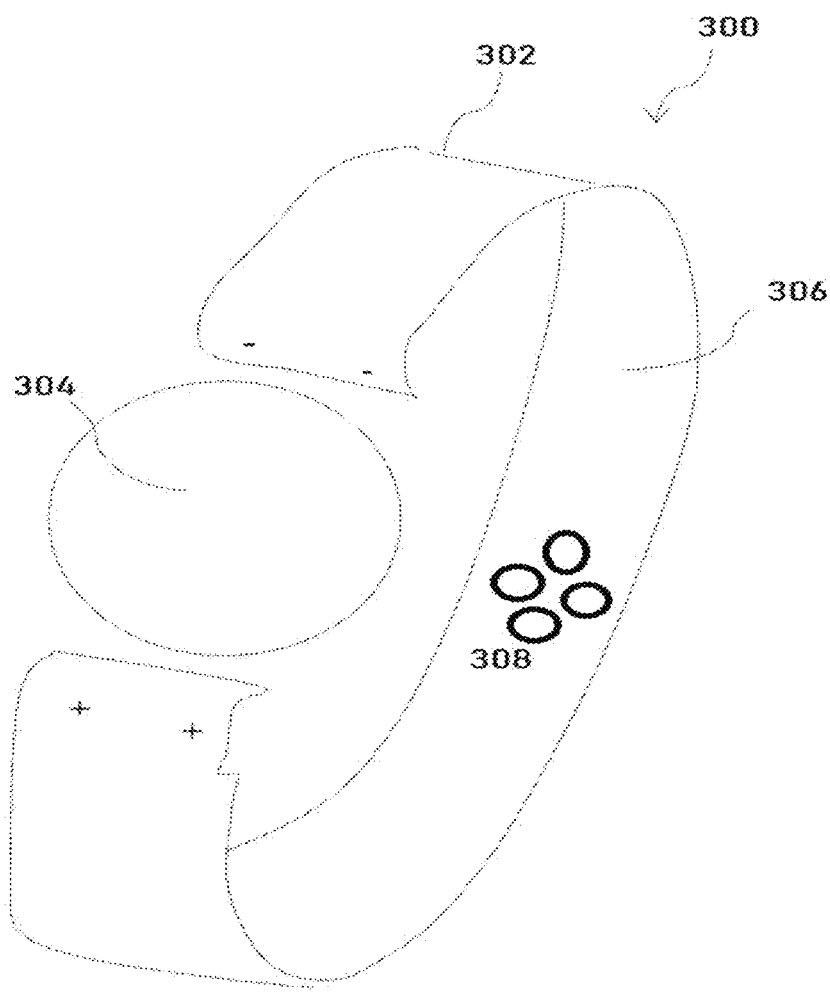

FIG. 2B

| |
|---|
| capturing continuously vital signs and motion data from one or more sensors adapted to be coupled to a user |
| capturing food consumption of the user |
| predicting a predetermined health condition of the user based on the vital signs; |
| generating a plan for the predetermined health condition |
| prompting the user to execute the plan with a closed-loop feedback based on sensor data |

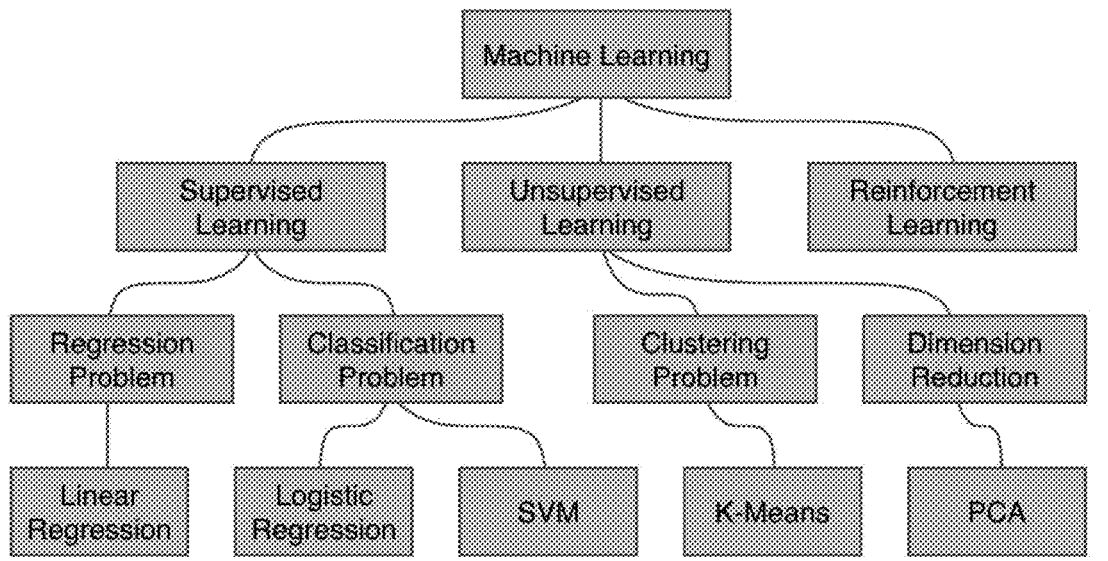
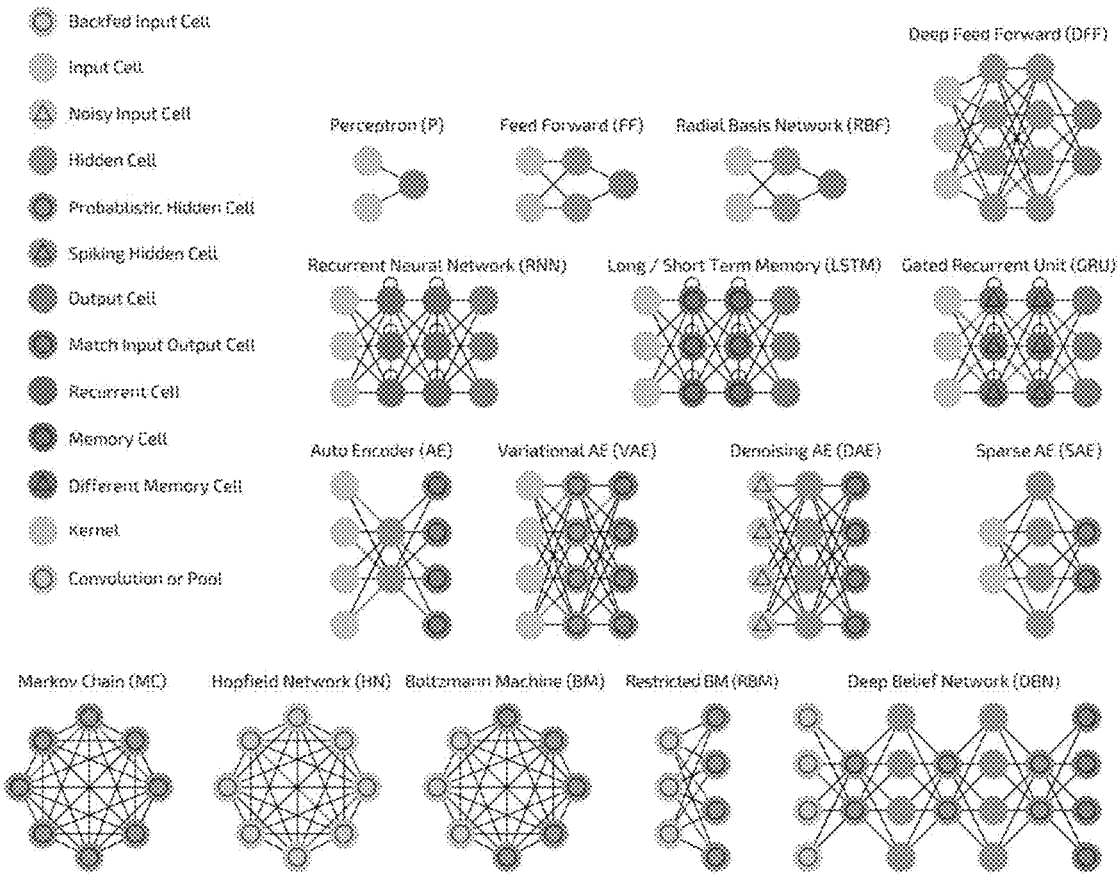
FIG. 6

HEALTH MANAGEMENT

BACKGROUND

The present invention relates to health management with sensors.

Synopsis

In one aspect, a method for health and fitness capturing continuously vital signs and motion data from one or more sensors adapted to be coupled to a user; capturing food consumption of the user; predicting a predetermined health condition of the user based on the vital signs; generating a plan for the predetermined health condition; and prompting the user to execute the plan with a closed-loop feedback based on sensor data.

Implementations may include one or more of the following. The predetermined health condition can be diabetes. The method may include one of: determining an effect of a predetermined food item on glucose; determining an effect of a second food item on glucose when taken with the predetermined food item; determining a glucose reduction when a selected activity is performed by the user; performing a physical activity within a selected period after a meal to keep glucose level in a predetermined range; presenting one or more activity options to the user to implement to keep the glucose level below a predetermined threshold; adjusting a timing or intensity of a selected physical activity to maintain a glucose target; or estimating glucose level using bio-impedance sensors. The method may include one of: measuring a user weight and determining a weight loss program; measuring user activity or exercise and determining a weight loss program; determining user smoking or drug dependency and weaning the user from smoking or drug through a series of behavioral changes including exercise. The predetermined health condition comprises high blood pressure. The method may include one of: a non-invasive blood pressure sensor to continuously estimate blood pressure in a closed-loop feedback; immediately reducing blood pressure with a diuretics, an angiotensin-converting enzyme (ACE) inhibitor, an angiotensin II receptor blocker (ARB), calcium channel blocker, alpha blocker, alpha-beta blocker, beta blocker, renin inhibitor, aldosterone antagonist, garlic or garlic extract pills to reduce blood pressure, music therapy, biofeedback, deep breathing, or exercise. A biofeedback sensor can be used reduce blood pressure in real time. The method may include one of: coaching the user to improve user health; wherein the coaching comprises social networking with people having user health characteristics; wherein the coaching provides feedback including adjusting positions to match a target posture; wherein the coaching provides motivation or encouragement; or wherein the coaching is customized for a particular user.

BRIEF DESCRIPTION OF THE DRAWINGS

FIG. 2A shows an exemplary wrist-band to house medical/health sensors and battery/power supply.

FIG. 2B shows an exemplary process to use sensors and software to keep a user healthy.

FIG. 6 shows exemplary AI systems to manage/coach user health.

DESCRIPTION

The configuration of an automated personal health coaching system is described. In some embodiments, a sensor device includes a set of one or more sensors configured to obtain vital signs and motion data samples, and one or more processors coupled to the set of sensors. The sensors can include ECG, optical heart rate, EMG, or bioimpedance sensors, among others. Preferably non-invasive sensor(s) are used. In some embodiments, the sensor device communicates with a local mobile device which performs management and local processing functions. Machine learning is used to model user diet, user activity, user medication, and user medical condition, and based on sensor feedback data, the machine learning recommends certain action(s) to be taken for the user to stay healthy. Based on the user health and predetermined sequences of food and physical activity, the user can be moved from a bad health state to a good health state using the sensor device in a close-loop feedback arrangement. Further, the sensor device can provide glanceable user health state by changing a color of a light visible to the user (red light may mean health problem, yellow light may mean check vital signs, green light may mean healthy condition, for example). The system can track user progress over time, leading to insufficient body metric measurement data for accurately characterizing user status and supporting users with personalized therapeutic interventions over time. The constant feedback from the sensors, along with social network (such as Facebook) peer support and/or coach support, helps improves user adherence.

Figure 1:
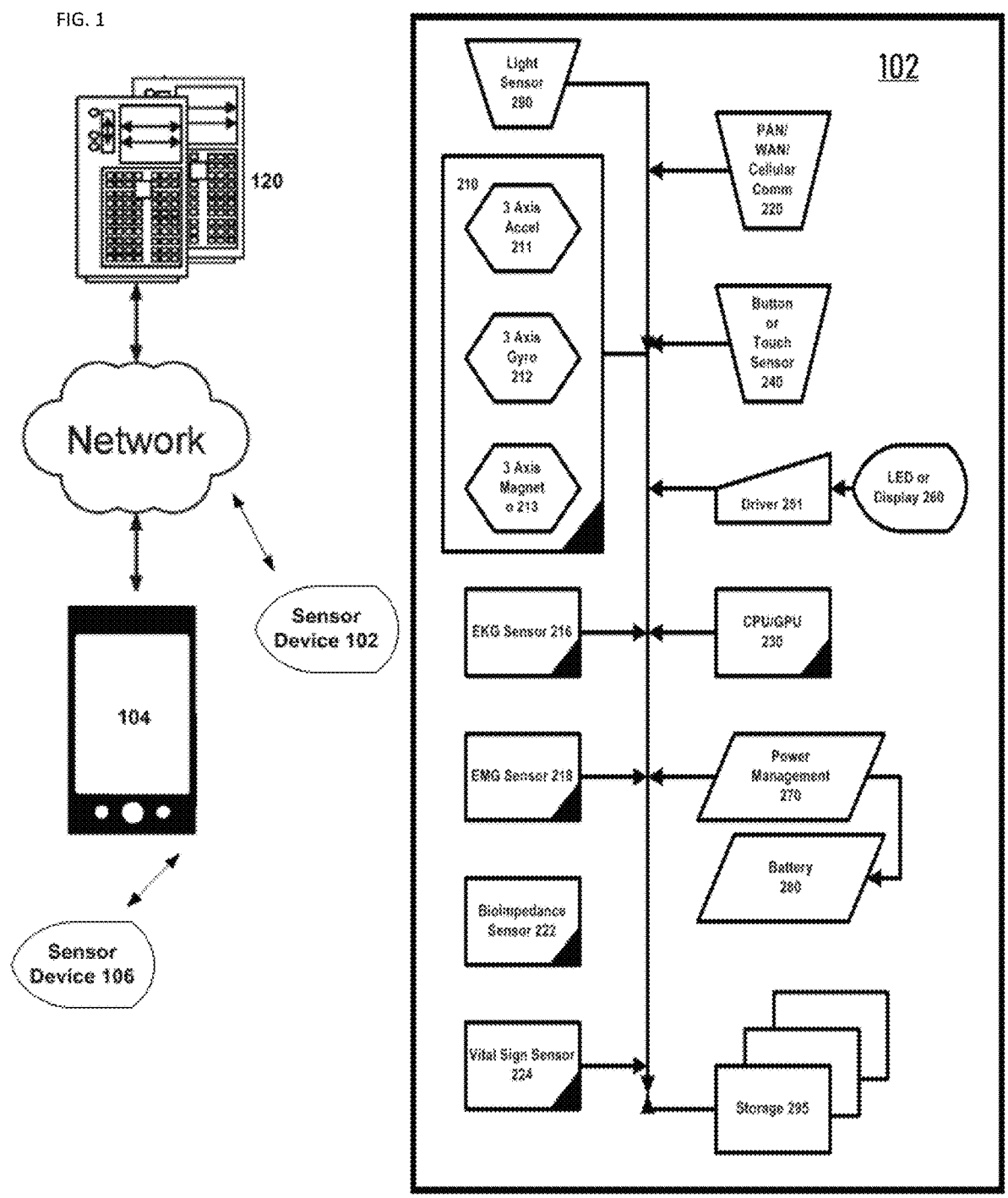
FIG. 1 shows an exemplary health sensing system.

First, the technology can confer improvements in the computational processing capabilities of components of the system of FIG. 1. For example, the technology can computationally determine user subgroups (e.g., based on demographics, physical activity characteristics, etc.) including users who progress through a group program together (e.g., to enable peer support for a health regimen), where the classification of users into subgroups can improve data storage, retrieval, and analysis of body metric measurement data collected for the users. In specific examples, collected body metric measurement data for users from a user subgroup can be stored in association with a user subgroup identifier; retrieved (e.g., in aggregate; for a subset of users of the user subgroup; etc.) based on user subgroup identifier (e.g., to improve retrieval speed for user subgroup-associated data); and processed in relation to the user subgroup to improve the accuracy of characterization and treatment of users within the user subgroup. In another example, the technology can improve the application of vital sign sensors, inertial sensors, and/or other suitable activity-related sensors as tools, such as through providing an expansive digital network wirelessly connecting medical improvement systems (e.g., remote servers), weight sensor subsystems, and/or motion sensor subsystems across populations of users to extend the applicability of activity-related sensors (e.g., biometric sensors, optical sensors, etc.) to digital environments including peer support (e.g., through user subgroups) and/or coach support (e.g., through enabling wireless communication between users and facilitators) for health regimens. As such, the technology can amount to an inventive distribution of functionality across a network for improving data aggregation, data processing, and/or user experience, such as through distributing data collection and automatic transmission functionality across a plurality of wireless weight sensor subsystems and/or wireless motion sensor subsystems assigned to (e.g., linked with corresponding user accounts) and provided to users within a user subgroup; and distributing data storage, retrieval, and/or analysis functionality and/or therapeutic intervention provision functionality to the medical improvement system for optimizing user progress tracking and user status improvement. The technology can thus provide a full-stack approach leading to improvements in healthcare costs and disease prevention (e.g., diabetes prevention).

Second, the technology can provide technical solutions necessarily rooted in computer technology (e.g., leveraging a medical improvement network including connected weight sensor subsystems with vital sign sensors; connected motion sensor subsystems with inertial sensors; remote servers; and/or other suitable components to enable a user subgroup to progress through a digitally administered program together; etc.) to overcome issues specifically arising with computer technology (e.g., enabling a digital network of non-generalized devices such as activity-related sensors; digitally providing peer support and/or coach support for users remote from each other; computationally determining and providing physical activity metrics and/or therapeutic interventions tailored for optimizing user adherence and improvement; etc.). In an example, the technology can apply computer-implemented rules (e.g., feature engineering rules for processing body metric measurement data into an operable form for extracting relevant physical activity metrics and/or therapeutic interventions in relation to users and corresponding user subgroups; etc.) in conferring improvements to the computer-related technical field of digital healthcare.

Third, the technology can improve the technical fields of at least computer networks, body metric measurement devices, digital healthcare, digital communication (e.g., between users, facilitators, etc.), and/or other relevant fields. The technology can continuously collect and utilize specialized datasets unique to network-enabled, non-generalized body metric measurement devices in order to better characterize and/or treat user statuses. Further, the technology can take advantage of such devices and datasets to better improve the understanding of correlations between user behaviors, physical activity metrics, and appropriate therapeutic interventions.

Fourth, the technology can transform entities (e.g., users, body metric measurement devices, specialized datasets collected from activity-related sensors, etc.) into different states or things. For example, the technology can identify therapeutic interventions to promote to a user for improving user statuses (e.g., in relation to weight, cardiovascular health, diabetes, etc.) thereby transforming the health of the user. In another example, the technology can activate, control, and/or otherwise interact with body metric measurement devices to promote therapeutic interventions (e.g., by generating control instructions for the device to execute), thereby transforming the physical activity-related devices.

Fifth, the technology can confer improvements in computer-related technology by facilitating performance of functions not previously performable, such as computer network-related functions that the technology can leverage to enable functionality of the medical improvement network of body metric measurement devices and remote medical improvement systems.

The technology can, however, provide any other suitable benefit(s) in the context of using non-generalized computer-related systems for supporting health regimens.

The following description of embodiments of the invention is not intended to limit the invention to these embodiments, but rather to enable any person skilled in the art to make and use this invention.

Monitoring Sensor(S)

FIG. 1 shows an exemplary system diagram, illustrating an embodiment of an automated health coaching system. In this example, one or more sensor devices 102 and 106 (also referred to as personal health coaching devices) are used to detect motion, medical parameters, or vital signs. As will be described in greater detail below, a sensor device includes one or more accelerometers, one or more gyroscopes, and optionally one or more magnetometers that are configured to take measurement data samples of acceleration, angular velocity, and optionally magnetic field, respectively, in connection with the motions of the device. A user wears one or more sensor device(s) during exercises (e.g., on the ankle while running, on arms and legs while swimming, etc.) to capture the user's motion data. For health monitoring, each sensor can include ECG, optical heart rate, EMG, or bio-impedance sensors, among others.

The data samples are processed to evaluate the user's fitness and health performance and optionally provide health feedback. In some embodiments, a sensor device includes a processor configured to perform the data processing, evaluation, and/or feedback. In some embodiments, the configurations of the sensor device to be shown on a display are also determined based on the data samples. Sensor data can be transmitted to a disease management server in a data center 120 by a long-range communication network such as a 5G transceiver, for example.

In some embodiments such as the example shown, the sensor devices are connected (e.g., via a wireless communication interface such as Bluetooth interface) to a local computing device 104, which can be a personal computer, a smartphone, a tablet, or any other appropriate computing device that is configured to perform the data processing, evaluation, and/or feedback. The management device executes one or more configurations and other related management applications to manage the configuration and operations of the sensor devices. In some embodiments, the management functions are performed by the sensor device directly. In some embodiments, the local device 104 (or the sensor device 102 if the sensor device directly performs processing) is optionally connected to a server 120 via a network such as the Internet. Data such as configuration, measurements, performance, etc. can be stored on the server to be accessed later and/or further processed.

In some embodiments, the local computer 104 (or the sensor device if the sensor device directly performs processing) is optionally connected to one or more cloud-based devices 120 via a network such as the Internet. Devices 120 (also referred to as the cloud computers) can include servers, storage devices, networking devices, and/or other appropriate networked elements that provide cloud-based computing services. Data such as configuration, measurements, performance, etc. can be stored on devices 120 to be accessed later and/or further processed.

One exemplary sensor device 102 includes an inertial magnetic unit (IMU) 210 which includes a 3-axis accelerometer 211, a 3-axis gyroscope 212, and a 3-axis magnetometer 213. IMU 210 is connected with a microcontroller unit (MCU) 230. In this example, sample measurement data collected by the IMU is offloaded to a management device to be further processed. MCU 230 sends and receives data gathered by the IMU through a communication interface 220, which can be Bluetooth LE or other wireless connection, with a management device such as a smart phone, tablet, or PC. In other embodiments, the sensor device optionally includes a processor that processes the sample measurement data. A storage element 295 is connected to MCU 230. The storage element can be implemented using read-only memory (ROM), non-volatile random-access memory (NVRAM) (e.g., flash), nano-RAM, or any other appropriate devices. The vital sign sensors such as EMG, EKG, bioimpedance, and optical heart rate monitors, among others, and the use of accelerometer for kinematic modeling of a person's movement or exercise pattern, are detailed in U.S. Pat. No. 9,820,658 to the instant inventor Bao Tran, the content of which is incorporated by reference.

The sensor's heart-rate pulse sensor can identify cardiac issues such as atrial fibrillation. The device 102 periodically checks for irregularities in the heart rate. One embodiment uses the optical sensors, while other embodiments use EKG sensors on the device 102.

The sensor can measure blood pressure (BP). Preferably the BP is cuffless using techniques such as Pulse Transit time or Arterial Tonometry, as detailed in U.S. Pat. No. 8,747,336 to the instant inventor, the content of which is incorporated by reference. Arterial tonometry based cuff-less blood pressure measurement can be done also where a non-invasive arterial tonometer is placed on the skin overlying a peripheral artery. Then, the sensor applies force to compress the artery against the underlying bone until the maximum pulse pressure is achieved. At that point, it can be assumed that the only force acting on the artery is the inward force of the tonometry sensor (Pt), the outward force of the intravascular blood pressure (Pa), and the wall tension of the underlying artery (T). The maximum pulse pressure occurs when the artery is compressed such that the wall tension force is directed perpendicularly to the tonometry sensor and blood pressure forces. Directing the wall tension perpendicularly ensures that the tonometric force measured by the sensor only represents the blood pressure of the underlying vessel. Pulse transit time (PTT) based cuff-less blood pressure measurement and to measure blood pressure, users place their index finger on the optical sensor on the back of the sensor 102 or local computer 104. PTT represents the time it takes for a pulse pressure wave to travel from its origin at the heart to a distal point. Since it is difficult to non-invasively measure a pulse waveform at the heart, the onset of the QRS complex is measured as a surrogate. The arrival of a pulse pressure wave at the finger or wrist can be measured using a photoplethysmography.

In another embodiment, a body temperature and sweating sensor, a respiratory rate sensor module, an environmental temperature and humidity sensor module, and a movement speed sensor module can be used. The body temperature and sweating sensor module is adapted to sense an early stage exhaustion signal by collecting information regarding monitoring body surface temperature, humidity and capillary contraction to monitor muscle exercise to determine whether the early stage exhaustion appears. Upon detecting the early stage exhaustion, an alert will be announced. The respiratory rate sensor is adapted to sense the respiration rate that is an important reference of the user's exercise state. The respiration rate in combination with other sensor information can determine whether hyperventilation appears and whether workout efficiency reduces. The respiratory rate can be used to determine whether the user needs to take a break. The environmental temperature and humidity sensor are adapted to sense the environmental temperature and humidity, which assists with setting the optimal exercise strength. The movement speed sensor is adapted to detect velocity, which can be used to understand the user's type of exercise and variability of workout efficiency during exercising, thereby allowing the module to provide suggestions for which type of exercise to engage.

One embodiment calculates the calories burned during a workout based on user height, weight, age, and data collected about the workout. Resting calories burned are calculated with the Harris-Benedict equation. From there, the user active minutes and workouts are added to get a total daily calorie burned. The bioimpedance sensor is used to estimate hydration and also to estimate glucose level, as detailed in the co-pending provisional application to the instant inventor, the content of which is incorporated by reference. Additionally, the system can include any one or more of: pedometers, weight scales, blood sugar monitors, blood pressure monitors, devices associated with EEG, EOG, EMG, ECG, thermometers, heart rate monitors, ambient environment devices (e.g., such as sensing and control systems for temperature, light, air quality and/or composition, etc.), medication devices (e.g., such as automatic medication dispensers; personal assistant devices; etc.), user devices (e.g., through which application-based therapeutic interventions, such as educational course components, can be promoted, etc.), coach devices, and/or any other suitable devices (e.g., biometric, medical and/or diagnostic devices, such as those configured to monitor and/or determine a wide variety of biometrics/biomarkers of an individual, etc.). In examples, treatment systems and/or other suitable system components can be used to receive or calculate biometric data about the user. The biometric data may include, for example, blood sugar values, heart beat values, blood pressure, temperature, weight, body mass index values, body fat percentage, hydration, and/or other biometric data.

The request sent by the disease management server may be in the form of surveys designed to collect particular information. The surveys may be targeted to collect information about a patient's dietary behavior (e.g., carbohydrate intake, portion control), self-monitoring of blood glucose, medication doses, physical activity, psychological status, alcohol intake, smoking activity, and any other information that might affect the patient's well-being such as blood lipid level, blood pressure, age, gender, height and weight, or race. The local computer 104 or the server at center 120 may prompt the user to enter information by displaying the survey and receiving the patient's responses to the questions posed in the survey. The scripts may also be designed to educate the user or to promote positive behavior/behavior modification by the user.

The device 102 can detect various health states of the user, for example, good, fair, or bad. To provide ambient visual feedback to the user, a particular color can be show to indicate the various health states. The sensor device 102 includes an LED 260 controlled by LED driver 251, which is coupled both with the LED's hardware interface and with MCU 230. In some embodiments, LED 260 includes an RGB LED. The LED driver implements various control functions such as turning the LED on and off, switching color, changing intensity, etc. The MCU can invoke these control functions using an application programming interface (API) (e.g., function calls or commands) provided by the LED driver maker. In various embodiments, configuration information can be generated by MCU 230, or be generated by the management device which forwards the configuration information to the sensor device via communication interface 220. In response to the configuration information, the MCU invokes corresponding API calls and causes the LED driver to send appropriate control signals to LED 260 to configure the LED's on/off state, color, intensity, etc. In some embodiments, LED Driver 251 is incorporated into MCU 230. While a light is used to provide ambient feedback, other mechanisms to provide feedback include a speaker to provide audio feedback, a video screen or a light to provide visual feedback, a haptic display to provide tactile feedback, and the like.

The sensor device also optionally includes a touchscreen or button 240. In various embodiments, the button is multifunctional and can be used as a power on switch/sleep mode activator or a general-purpose user interface button. The sensor device also optionally includes a light sensor and LED 290, which is configured to detect different types of mounting chassis on which the device is mounted. The sensor device 102 also includes a battery 280 or other appropriate power source. The voltage delivered to the other parts of the sensor device is delivered through power management module 270. One embodiment uses rechargeable battery that can be recharged using a USB charging cable for example, but for long operation a user replaceable lithium coin cell such as a CR2032-type coin cell can be used, for example.

In some embodiments, the sensor device includes an LED (e.g., an RGB LED) that is configurable to emit different colors of light depending on RGB values input into the LED's device interface to provide glanceable, ambient awareness of the user's health status. In one embodiment where the device has an LED perimeter ring is provided with red color as being dangerous condition if dangerous conditions exist, and green color is user health is great, and yellow color for potential issues. Thus, the user can quickly assess his/her health condition without having to look up the detailed numbers unless a red condition exists. in some embodiments where red is viewed as a good luck sign and no danger, the user can also specify a custom color other than the default color options by specifying a color code. The color code can be a standard color representation such as a set of RGB values or a custom color code (e.g., blue=1, green=2, purple=3, etc.). Other color code representations such as a set of HSL values, an HTML color code, etc., can also be used. The user can specify the color code directly, or select from a color wheel or chart showing additional color options. In some embodiments, an additional user interface (not shown) is provided for the user to enter an identifier for the sensor device.

The color specification and/or sensor identifier information entered by the user is sent by the local computer 104 to the sensor device via the communications interface between the devices (e.g., the Bluetooth interface), according to a predefined communication protocol. In some embodiments, a proprietary byte-based protocol format is used, where the message fields include identifier, action, data, etc. The possible values of the action field correspond to set, erase, reboot, etc. In some embodiments, the configuration application formats the configuration message comprising the sensor identifier, action, the color indication (which can be a color code or a command to set the LED to a specific color), etc., and invokes a custom protocol call to output the message via the local computer's communication interface. In embodiments where the communication interface is Bluetooth, the custom protocol call can be implemented using the Bluetooth SDK. The message is transmitted to the sensor device's communication interface and further processed by the MCU. In response to receiving the configuration information, the MCU of the sensor device invokes appropriate API calls to the device driver to set the color according to the user's configuration, and causes a control signal to be sent to the LED. In response to the control signal, the LED will emit a color (e.g., blue) corresponding to the configuration. The configuration information is stored locally on the storage element of the sensor device.

In some embodiments, the CPU/GPU can be an MPU with low processing power; thus, each time the sensor gets new data, the EKG data, the EMG data, the bio-impedance data, or the raw measurement data from the IMU is communicated from the sensor device to the local computer according to a pre-specified protocol. The local computer computes the orientation, state, and/or color information, and sends a set color message back to the sensor device to configure the LED color. The local computer further updates the configuration application to display a color that matches the color set on the sensor device. The orientation, state, and/or color information is stored on the local computer.

In some embodiments, the CPU/GPU has sufficient processing power to compute the health data, device orientation, state, and color information. Thus, the state/color computation is performed on the sensor device locally, the LED color is reset according to the results, and the results (e.g., orientation, state, and/or color information) are sent to the local computer according to a pre-specified protocol. Upon receiving the results, the local computer updates the configuration application to display a matching color. In yet other embodiments, the CPU/GPU stores verbal coaching instructions in memory, and based on sensor data, sends the coaching instructions in real-time to an audio device (such as earbuds or headphones or speakers) wirelessly coupled to the CPU/GPU to verbally coach the user to increase exercise performance and/or handle particular health condition.

FIG. 2A shows an exemplary wrist-band to house sensors and power supply while FIG. 2B shows an exemplary process to use sensors and software to keep a user healthy. FIG. 2A shows a watch 304 that can be a smart watch receiving power and sensor data from the wrist band, where the smart watch with battery in the band enables smart watch operation with extended duration such as a week or month without recharging, for example. Alternatively, the watch can be a conventional analog watch such as a Rolex watch commonly worn for fashion reasons, which is adapted with a smart watchband that includes wireless sensors and processing to monitor health. The conventional analog watch can be configured to be coupled to the wrist band 302 including a flexible battery integrated therein. While the flexible battery described herein can be flexible lithium, prismatic, or cylindrical battery cell, it is contemplated that such a battery is fabricated with flexible material which is further adapted to function as the wrist band 302 or otherwise as a belt for attaching the watch 300 to a user. The wrist band 302 includes a flexible battery portion 306 to integrate the battery therein to power various sensors 308 as detailed above (for example, ECG, bioimpedance, accelerometer, and other sensors embedded in the wristband 302. In one embodiment, the sensors are mounted on the patient's wrist (such as a wrist or ankle wearable device sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others. The sensor can also include an indoor positioning system or alternatively a global position system (GPS) receiver that relays the position and ambulatory patterns of the patient to the server for mobility tracking. In one embodiment, the sensors for monitoring vital signs are enclosed in the wrist band. The sensors can be attached to the back of the case. While bioimpedance based glucose estimation is used, other means of detecting glucose can be used. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the wearable device. In another embodiment, EKG/ECG contact points are positioned on the back of the wrist-wearable device case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters. These sensors are coupled to the CPU/GPU and powered by the flexible battery. The positive and negative portions of the battery portion 306 are electrically coupled to the watch 300. The terminals are also adapted to electrically and mechanically couple the battery to a charging device. The flexible battery unit can be configured to be connected to the control circuit electrically. In the third embodiment, the flexible battery unit may be provided with the flexibility through the interconnection of individual elements. The flexible battery unit can include a plurality of battery flexible sub-units 302 connecting flexible circuit elements, which are disposed between the battery flexible sub-respectively to connect the battery flexible sub-units physically and electrically. In one embodiment, the flexible electronic controller further includes a power supply which is constructed and arranged to provide power to the flexible electronic circuitry. In some arrangements, the power supply generates power (e.g., due to a chemical reaction). In some arrangements, the power supply stores power from a main power feed (e.g., a rechargeable battery storing a charge). Gel, chemicals, or physical batteries are examples of power supplies which are capable of being used in these arrangements. In some arrangements, the power supply derives power from the environment, e.g., the power supply includes photovoltaic cells that respond to light and/or power generators that respond to heat and/or vibration. Alternatively, the power supply can capture body heat and convert body heat into energy to power the sensors. To further reduce power consumption, a remote system can beam power to the sensors. For example, WiFi or 5G transceivers in a room can beam power to the wristband to keep sensors operating while keeping wristband very thin for fashion and comfort reasons. In one system, a dual-band circularly polarized rectenna at 1.85 and 2.45 GHz uses a single antenna and a single RF-to-dc rectifier. The circuit contains a dual-band circularly polarized antenna and a dual-band RF-to-dc rectifier based on a miniaturized 180° hybrid ring junction. The ring junction is used to independently match the subrectifiers at each frequency. The rectenna was tested with single-tone and multi-tone incident waves. It achieves more than 300 mV and 40% efficiency, across a 4-kΩ resistive load, at very low power density of 1.13 µW/cm2 at 1.85 GHz and 1.87 µW/cm2 at 2.45 GHz. It also achieves more than 150 mV under the same load condition and in the critical case when receiving only one of the two frequency bands. It is dedicated to harvest RF energy in the GSM 1800 and the 2.45-GHz ISM bands, regardless the polarization angle of the incident waves.

The wristband 302 can also incorporate on the outside of the flexible battery a flexible display which may be formed from multiple layers of material. These layers may include a touch sensor layer such as a layer on which a pattern of indium tin oxide (ITO) electrodes or other suitable transparent electrodes have been deposited to form a capacitive touch sensor array. These layers may also include a layer that contains an array of display pixels. The touch sensor layer and the display layer may be formed using flexible sheets of polymer or other substrates having thicknesses of 10 microns to 0.5 mm or other suitable thicknesses (as an example).

The display pixel array may be, for example, an organic light-emitting diode (OLED) array. Other types of flexible display pixel arrays may also be formed (e.g., electronic ink displays, etc.). The use of OLED technology to form flexible display is sometimes described herein as an example. This is, however, merely illustrative. Flexible display may be formed using any suitable flexible display technology. The use of flexible displays that are based on OLED technology is merely illustrative.

In addition to these functional display layers (i.e., the OLED array and the optional touch sensor array), display may include one or more structural layers. For example, display may be covered with a flexible or rigid cover layer and/or may be mounted on a support structure (e.g., a rigid support). Layers of adhesive may be used in attaching flexible display layers to each other and may be used in mounting flexible display layers to rigid and flexible structural layers.

In configurations for display in which the cover layer for display is flexible, input-output components that rely on the presence of flexible layers may be mounted at any suitable location under the display (e.g., along peripheral portions of the display, in a central portion of the display, etc.). In configurations for display in which the flexible layers are covered by a rigid cover glass layer or other rigid cover layer, the rigid layer may be provided with one or more openings and the electronic components may be mounted under the openings. Device may also have other openings (e.g., openings in display and/or housing for accommodating volume buttons, ringer buttons, sleep buttons, and other buttons, openings for an audio jack, data port connectors, removable media slots, etc.).

The flexible display may be formed by stacking multiple layers including flexible display layer, touch-sensitive layer, and cover layer. Flexible display may also include other layers of material such as adhesive layers, optical films, or other suitable layers. Flexible display layer 14 may include image pixels formed form light-emitting diodes (LEDs), organic LEDs (OLEDs), plasma cells, electronic ink elements, liquid crystal display (LCD) components, or other suitable image pixel structures compatible with flexible displays.

Touch-sensitive layer may incorporate capacitive touch electrodes such as horizontal transparent electrodes and vertical transparent electrodes. Touch-sensitive layer may, in general, be configured to detect the location of one or more touches or near touches on touch-sensitive layer based on capacitive, resistive, optical, acoustic, inductive, or mechanical measurements, or any phenomena that can be measured with respect to the occurrences of the one or more touches or near touches in proximity to touch sensitive layer.

Software and/or hardware may be used to process the measurements of the detected touches to identify and track one or more gestures. A gesture may correspond to stationary or non-stationary, single or multiple, touches or near touches on touch-sensitive layer 14B. A gesture may be performed by moving one or more fingers or other objects in a particular manner on touch-sensitive layer 14B such as tapping, pressing, rocking, scrubbing, twisting, changing orientation, pressing with varying pressure and the like at essentially the same time, contiguously, or consecutively. A gesture may be characterized by, but is not limited to a pinching, sliding, swiping, rotating, flexing, dragging, or tapping motion between or with any other finger or fingers. A single gesture may be performed with one or more hands, by one or more users, or any combination thereof.

Cover layer may be formed from plastic or glass (sometimes referred to as display cover glass) and may be flexible or rigid. If desired, the interior surface of peripheral inactive portions of cover layer may be provided with an opaque masking layer on such as black ink. Touch-sensitive flexible display section may be formed from display pixel array layer and optional touch sensor layer. Pressure may cause flexible display to temporarily deform outward of the wearable device such as the watch. Pressure may, if desired, be formed by an internal actuator that deforms display to provide a desired tactile sensation on the surface of display to a user. Flexible display may have a natural resiliency that, following deformation causes flexible display to temporarily deform outward of the watch before returning to its natural shape. Internal component may be a button, an actuator such as a motor, solenoid, vibrator, or piezoelectric actuator, a pressure sensor, an audio component such as a microphone or speaker, or other component. Because display is flexible, these components may operate effectively, even when covered by display. For example, audio components such as microphones and speakers may receive and transmit sound through flexible display. A barometric pressure sensor or a force sensor may also receive input through flexible display. Components such as actuators may be used to temporarily create raised ridges or other external features on the surface of the flexible display (e.g., to indicate to a user where an on-screen button or group of buttons is located).

In one embodiment, touch-sensitive flexible display section may be deformed to depress a dome switch, thereby activating the switch (e.g., shorting internal switch terminals together to close the switch). In these embodiments, the flexible display can form an array of dome switches that provide tactile feedback to typists. The use of a dome switch with a dome-shaped biasing structure is merely illustrative and other switch shapes such as rectangular shaped like a keyboard switch can be done. When an active display portion is configured so as to overlap buttons and other components, there is generally more area available for the active display portion. The presence of flexible display over button may also reduce the risk of moisture or dirt entering into the interior of device. An actuator such as a piezoelectric actuator can be used to detect actuation and/or provide tactile feedback. The actuator may vary in shape (e.g., thickness) in response to applied control voltages and may produce an output voltage when compressed (i.e., the piezoelectric element in actuator may serve as a force sensor in addition to serving as a controllable actuator). A user may exert force on flexible display in a direction. Flexible display may be deformed to exert a mechanical pressure on piezoelectric element or other force sensor, inducing a voltage which may be transmitted to the wearable device. Conversely, piezoelectric actuator may be used to provide tactile feedback to a. A voltage difference applied to the surfaces of piezoelectric actuator may induce an expansion of piezoelectric actuator 90. Piezoelectric actuator may then deform flexible display for providing tactile feedback to a user. A touch sensor array associated with display may be used to gather user input (i.e., the touch sensor array may be used to determine when a user has pressed the virtual key associated with portion). The location of portion may also be indicated visually using associated display pixels in flexible display. At times, a user may desire to be able to locate portion without having to look at flexible display. Deforming flexible display in the vicinity of portion using structural component may allow a user to locate portion without visual aid. Structural component may be an isolated component indicating the location of a single portion of touch-sensitive layer or may be one of various components indicating the locations of an array of portions (e.g., the array of letter, number, and symbol keys in a virtual keypad displayed on display). Structural component may be a separate component mounted to support structures or may be an integral part of support structures. The location of interface component may be indicated visually using display pixels in flexible display. The deformation of flexible display in the vicinity of interface component using structural component may also allow the user to locate interface component without visual aid. A ridge or other deformation such as deformation in flexible display may be used to indicate the location of button.

The wearable device includes bioelectrical impedance (BI) spectroscopy sensors in addition to or as alternates to EKG sensors and heart sound transducer sensors. BI spectroscopy is based on Ohm's Law: current in a circuit is directly proportional to voltage and inversely proportional to resistance in a DC circuit or impedance in an alternating current (AC) circuit. Bioelectric impedance exchanges electrical energy with the patient body or body segment. The exchanged electrical energy can include alternating current and/or voltage and direct current and/or voltage. The exchanged electrical energy can include alternating currents and/or voltages at one or more frequencies. For example, the alternating currents and/or voltages can be provided at one or more frequencies between 100 Hz and 1 MHz, preferably at one or more frequencies between 5 KHz and 250 KHz. A BI instrument operating at the single frequency of 50 KHz reflects primarily the extra cellular water compartment as a very small current passes through the cell. Because low frequency (<1 KHz) current does not penetrate the cells and that complete penetration occurs only at a very high frequency (>1 MHz), multi-frequency BI or bioelectrical impedance spectroscopy devices can be used to scan a wide range of frequencies.

In a tetrapolar implementation, two electrodes on the wrist wearable device or wrist band are used to apply AC or DC constant current into the body or body segment. The voltage signal from the surface of the body is measured in terms of impedance using the same or an additional two electrodes on the wearable device or wrist band. In a bipolar implementation, one electrode on the wrist wearable device or wrist band is used to apply AC or DC constant current into the body or body segment. The voltage signal from the surface of the body is measured in terms of impedance using the same or an alternative electrode on the wearable device or wrist band. The system may include a BI patch that wirelessly communicates BI information with the wrist wearable device. Other patches can be used to collect other medical information or vital parameter and communicate with the wrist wearable device or base station or the information could be relayed through each wireless node or appliance to reach a destination appliance such as the base station, for example. The system can also include a head-cap that allows a number of EEG probes access to the brain electrical activities, EKG probes to measure cranial EKG activity, as well as BI probes to determine cranial fluid presence indicative of a stroke. As will be discussed below, the EEG probes allow the system to determine cognitive status of the patient to determine whether a stroke had just occurred, the EKG and the BI probes provide information on the stroke to enable timely treatment to minimize loss of functionality to the patient if treatment is delayed.

Bipolar or tetrapolar electrode systems can be used in the BI instruments. Of these, the tetrapolar system provides a uniform current density distribution in the body segment and measures impedance with less electrode interface artifact and impedance errors. In the tetrapolar system, a pair of surface electrodes is used as current electrodes to introduce a low intensity constant current at high frequency into the body. A pair of electrodes measures changes accompanying physiological events. Voltage measured across is directly proportional to the segment electrical impedance of the human subject. Circular flat electrodes as well as band type electrodes can be used. In one embodiment, the electrodes are in direct contact with the skin surface. In other embodiments, the voltage measurements may employ one or more contactless, voltage sensitive electrodes such as inductively or capacitively coupled electrodes. The current application and the voltage measurement electrodess in these embodiments can be the same, adjacent to one another, or at significantly different locations. The electrode(s) can apply current levels from uA to 10 mA rms at a frequency range of ~100 KHz. A constant current source and high input impedance circuit is used in conjunction with the tetrapolar electrode configuration to avoid the contact pressure effects at the electrode-skin interface.

The BI sensor can be a Series Model which assumes that there is one conductive path and that the body consists of a series of resistors. An electrical current, injected at a single frequency, is used to measure whole body impedance (i.e., wrist to ankle) for the purpose of estimating total body water and fat free mass. Alternatively, the BI instrument can be a Parallel BI Model In this model of impedance, the resistors and capacitors are oriented both in series and in parallel in the human body. Whole body BI can be used to estimate TBW and FFM in healthy subjects or to estimate intracellular water (ICW) and body cell mass (BCM). High-low BI can be used to estimate extracellular water (ECW) and total body water (TBW). Multi-frequency BI can be used to estimate ECW, ICW, and TBW; to monitor changes in the ECW/BCM and ECW/TBW ratios in clinical populations. The instrument can also be a Segmental BI Model and can be used in the evaluation of regional fluid changes and in monitoring extra cellular water in patients with abnormal fluid distribution, such as those undergoing hemodialysis. Segmental BI can be used to measure fluid distribution or regional fluid accumulation in clinical populations. Upper-body and Lower-body BI can be used to estimate percentage BF in healthy subjects with normal hydration status and fluid distribution. The BI sensor can be used to detect acute dehydration, pulmonary edema (caused by mitral stenosis or left ventricular failure or congestive heart failure, among others), or hyper-hydration cause by kidney dialysis, for example. In one embodiment, the system determines the impedance of skin and subcutaneous adipose tissue using tetrapolar and bipolar impedance measurements. In the bipolar arrangement the inner electrodes act both as the electrodes that send the current (outer electrodes in the tetrapolar arrangement) and as receiving electrodes. If the outer two electrodes (electrodes sending current) are superimposed onto the inner electrodes (receiving electrodes) then a bipolar BIA arrangement exists with the same electrodes acting as receiving and sending electrodes. The difference in impedance measurements between the tetrapolar and bipolar arrangement reflects the impedance of skin and subcutaneous fat. The difference between the two impedance measurements represents the combined impedance of skin and subcutaneous tissue at one or more sites. The system determines the resistivities of skin and subcutaneous adipose tissue, and then calculates the skinfold thickness (mainly due to adipose tissue).

Various BI analysis methods can be used in a variety of clinical applications such as to estimate body composition, to determine total body water, to assess compartmentalization of body fluids, to provide cardiac monitoring, measure blood flow, dehydration, blood loss, wound monitoring, ulcer detection and deep vein thrombosis. Other uses for the BI sensor includes detecting and/or monitoring hypovolemia, hemorrhage or blood loss. The impedance measurements can be made sequentially over a period of in time; and the system can determine whether the subject is externally or internally bleeding based on a change in measured impedance. The wearable device can also report temperature, heat flux, vasodilation and blood pressure along with the BI information.

In one embodiment, the BI system monitors cardiac function using impedance cardiography (ICG) technique. ICG provides a single impedance tracing, from which parameters related to the pump function of the heart, such as cardiac output (CO), are estimated. ICG measures the beat-to-beat changes of thoracic bioimpedance via four dual sensors applied on the neck and thorax in order to calculate stroke volume (SV). By using the resistivity $\rho$ of blood and the length L of the chest, the impedance change $\Delta Z$ and base impedance (Zo) to the volume change $\Delta V$ of the tissue under measurement can be derived as follows:

The impedance cardiographic embodiment allows hemodynamic assessment to be regularly monitored to avoid the occurrence of an acute cardiac episode. The system provides an accurate, noninvasive measurement of cardiac output (CO) monitoring so that ill and surgical patients undergoing major operations such as coronary artery bypass graft (CABG) would benefit. In addition, many patients with chronic and comorbid diseases that ultimately lead to the need for major operations and other costly interventions might benefit from more routine monitoring of CO and its dependent parameters such as systemic vascular resistance (SVR).

In one embodiment to monitor heart failure, an array of BI sensors are place in proximity to the heart. The array of BI sensors detect the presence or absence, or rate of change, or body fluids proximal to the heart. The BI sensors can be supplemented by the EKG sensors. A normal, healthy, heart beats at a regular rate. Irregular heartbeats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

In one implementation, BIA measurements can be made using an array of bipolar or tetra polar electrodes that deliver a constant alternating current at 50 KHz frequency. Whole body measurements can be done using standard right-sided. The ability of any biological tissue to resist a constant electric current depends on the relative proportions of water and electrolytes it contains, and is called resistivity (in Ohms/cm 3). The measuring of bioimpedance to assess congestive heart failure employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. The resistance is impedance measured using direct current or alternating current (AC) which can flow through capacitors.

In one embodiment, a belt is worn by the patient with a plurality of BI probes positioned around the belt perimeter. The output of the tetrapolar probes is processed using a second-order Newton-Raphson method to estimate the left and right-lung resistivity values in the thoracic geometry. The locations of the electrodes are marked. During the measurement procedure, the belt is worn around the patient's thorax while sitting, and the reference electrode is attached to his waist. The data is collected during tidal respiration to minimize lung resistivity changes due to breathing, and lasts approximately one minute. The process is repeated periodically and the impedance trend is analyzed to detect CHF. Upon detection, the system provides vital parameters to a call center and the call center can refer to a physician for consultation or can call 9-1-1 for assistance.

In one embodiment, an array of noninvasive thoracic electrical bioimpedance monitoring probes can be used alone or in conjunction with other techniques such as impedance cardiography (ICG) for early comprehensive cardiovascular assessment and trending of acute trauma victims. This embodiment provides early, continuous cardiovascular assessment to help identify patients whose injuries were so severe that they were not likely to survive. This included severe blood and/or fluid volume deficits induced by trauma, which did not respond readily to expeditious volume resuscitation and vasopressor therapy. One exemplary system monitors cardiorespiratory variables that served as statistically significant measures of treatment outcomes: Qt, BP, pulse oximetry, and transcutaneous Pot (Ptco2). A high Qt may not be sustainable in the presence of hypovolemia, acute anemia, pre-existing impaired cardiac function, acute myocardial injury, or coronary ischemia. Thus a fall in Ptco2 could also be interpreted as too high a metabolic demand for a patient's cardiovascular reserve. Too high a metabolic demand may compromise other critical organs. Acute lung injury from hypotension, blunt trauma, and massive fluid resuscitation can drastically reduce respiratory reserve.

One embodiment that measures thoracic impedance (a resistive or reactive impedance associated with at least a portion of a thorax of a living organism). The thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive). A low intravascular fluid tension in the thorax ("thoracic hypotension") may result from changes in posture. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright. The accelerometer can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

In an embodiment to monitor wounds such as diabetic related wounds, the conductivity of a region of the patient with a wound or is susceptible to wound formation is monitored by the system. The system determines healing wounds if the impedance and reactance of the wound region increases as the skin region becomes dry. The system detects infected, open, interrupted healing, or draining wounds through lower regional electric impedances. In yet another embodiment, the bioimpedance sensor can be used to determine body fat. In one embodiment, the BI system determines Total Body Water (TBW) which is an estimate of total hydration level, including intracellular and extracellular water; Intracellular Water (ICW) which is an estimate of the water in active tissue and as a percent of a normal range (near 60% of TBW); Extracellular Water (ECW) which is water in tissues and plasma and as a percent of a normal range (near % of TBW); Body Cell Mass (BCM) which is an estimate of total pounds/kg of all active cells; Extracellular Tissue (ECT)/Extracellular Mass (ECM) which is an estimate of the mass of all other non-muscle inactive tissues including ligaments, bone and ECW; Fat Free Mass (FFM)/Lean Body Mass (LBM) which is an estimate of the entire mass that is not fat. It should be available in pounds/kg and may be presented as a percent with a normal range; Fat Mass (FM) which is an estimate of pounds/kg of body fat and percentage body fat; and Phase Angle (PA) which is associated with both nutrition and physical fitness.

An exemplary method to conveniently measure blood glucose level includes using an invasive glucose system to generate medical grade data to calibrate a mobile device with noninvasive sensors tracking the user's glucose level. The most accurate reading of a blood sugar level is measured directly from blood, using a glucose meter. The data from the glucose meter is provided to calibrate the non-invasive system. The method then includes generating a calibration curve based on a variety of user conditions (sleep, exercise, rest, sit, walk); and in real time detecting the user condition and applying the calibration curve to accurately estimate the glucose level.

The system guides the user in timing of calibration. Calibration, where necessary, are avoided when trend arrows indicate rapid swings in glucose. While systems are becoming more reliable, patients should be instructed when to verify sensor readings before taking action such as meal boluses or treatment of hypoglycemia.

Another process includes: using an invasive glucose system to generate medical grade data to calibrate a mobile device with noninvasive sensor(s) tracking the user's glucose level (for example the noninvasive sensors include at least a near-infrared light and a bioimpedance sensor); training a system to estimate glucose based on a variety of user conditions (sleep, exercise, rest, sit, walk) using best fit approach, statistical approach, or learning machine approach; in real time detecting the user condition with the non-invasive sensor(s) and applying the trained system to accurately and non-invasively estimate the glucose level.

Yet another process includes: using an invasive glucose system to generate medical grade data to calibrate a mobile device with one or more noninvasive sensor(s) tracking the user's glycemic index (GI) level (for example the noninvasive sensors include at least a near-infrared light and a bioimpedance sensor); training a system to estimate glucose based on a variety of user conditions (sleep, exercise, rest, sit, walk) using best fit approach, statistical approach, or learning machine approach; in real time applying the trained system to accurately and non-invasively estimate the GI for food consumption and optionally estimating calorie consumption.

A further process includes: using a non-invasive system with one or more noninvasive sensor(s) tracking the user's glycemic index (GI) level (for example the noninvasive sensors include at least a near-infrared light and a bioimpedance sensor); training a system to estimate GI that may take into consideration a variety of user conditions (sleep, exercise, rest, sit, walk) using best fit approach, statistical approach, or learning machine approach; in real time applying the trained system to accurately and non-invasively estimate the GI for food consumption and optionally estimating calorie consumption.

Another process includes: train a calorie estimator from a food database including images, food ingredient, calorie data using best fit approach, statistical approach, or learning machine approach; taking images of a food about to be consumed and matching the images to an entry in the food database with corresponding calorie data using image processing and the calorie estimator; determining quantity/type of food from the images; in real time applying the calorie estimator for estimating calorie consumption.

Yet another process includes: train a calorie estimator from a food database including images, food ingredient, calorie data using best fit approach, statistical approach, or learning machine approach; taking images of a food about to be consumed and matching the images to an entry in the food database with corresponding calorie data using image processing and the calorie estimator; determining quantity/type of food from the images; in real time applying the calorie estimator for estimating calorie consumption and GI based on the food ingredient.

A further process includes: train a calorie estimator from a food database including images, food ingredient, calorie data using best fit approach, statistical approach, or learning machine approach; taking images of a food about to be consumed and determining quantity/type of food from the images using image processing and the calorie estimator; using one or more noninvasive sensors (such as a near-infrared light, a bioimpedance sensor, a cornea based sensor, or suitable noninvasive sensor combinations) to determine the user's glycemic index (GI) level; applying the calorie estimator and the non-invasive sensor(s) to accurately and non-invasively estimate the GI for food consumption and/or estimating calorie consumption.

In one embodiment, a partially-invasive glucose sensor such as a continuous glucose monitoring (CGM) system from IF sampling (for example a Dexcom 4) can be used. The CGM unit needs to be calibrated with a validated starting glucose value. The blood sugar level measured directly from blood with the glucose meter is provided to calibrate the CGM system. The Dexcom CGM utilizes a glucose oxidase sensor at the tip of a wire that is implanted in the subcutaneous space. The G4 sensor is inserted via a dedicated applicator by the user or clinician just under the skin where it is held in place by an adhesive to the skin. The transmitter is snapped into a platform located on top of the sensor. The data are transmitted wirelessly and are displayed on a separate receiver. This device is FDA approved to provide glucose readings for 168 hours or 7 days. The device is calibrated every 12 hours.

In other embodiments, minimally-invasive sensors harvest interstitial fluid from the body to measure with an external non-implanted sensor are being developed that disrupt the skin barrier and trap the fluid that rises to the surface (reverse iontophoresis). A patch can be placed on the abdomen or extremity that passes a small electric current through the skin to draw a measurable amount of interstitial fluid. These embodiments then analyze the interstitial fluid in the same manner as the Dexcom 4 units discussed above.

In non-invasive embodiments, glucose sensors utilizing near infrared, impedance, occlusion, Raman or radio wave spectroscopy on the wrist, finger, abdomen, or earlobe are completely noninvasive. Noninvasive glucose monitoring depends either upon on the application of optical energy into tissue followed by measurement of the interaction of the optical energy with glucose in the intravascular, interstitial fluid, and intracellular compartments, or else measurement of a physiologic phenomenon which is proportionate to the blood glucose level. The optical energy is typically applied to an appendage, such as a fingertip, an earlobe, or a forearm.

One noninvasive embodiment uses infrared light spectroscopy to measure reflection of infrared light from the skin in proportion to the glucose concentration, and distinguishes the signal of water from that of glucose which is much smaller, as well as other potential interferents in the skin. Another embodiment applies optical energy to the buccal mucosa within the mouth because this region contains no stratum corneum, the outermost dead layer of skin, to absorb the optical energy. Yet another embodiment applies to the anterior chamber of the eye various types of optical energy. Another noninvasive embodiment applies ultrasonic, electromagnetic, and thermal methods to detect glucose-related shifts in earlobe tissue. Another embodiment determines glucose from analysis of acetone and other metabolites in the breath, a process that would potentially bypass the interfering effects of skin components and microcirculation present with other methods.

In one embodiment, a plurality of LEDs can be used, each individually activated so as to emit corresponding wavelengths in sequence. In a particular embodiment, the temperature sensors measure the temperature of the LEDs, the body temperature, and the temperature of the photodiode detectors. The accelerometer indicates the sensor orientation and movement and is used by the signal processor in determining valid plethysmographs. A neural network is used to match glucose related composite parameters. Clinical data collection compares invasive blood draw measurements to noninvasive sensor measurements of the same person. Neural networks or statistical analyzers predict composite parameters CPs derived noninvasively from sensor data. The clinical data collection derives an invasive blood panel that generates a myriad of blood constituents such as blood urea nitrogen (BUN), high-density lipoprotein (HDL), low-density lipoprotein (LDL), total hemoglobin (THB), creatine (CRE) to name just a few. Data collection then assembles parameter combinations from the blood constituents so as to derive composite parameters which are then tested with the predicted composite parameters. In the neural network, the particular weights for a selected parameter is stored in weights of the network, and for statistical analyzers, the parameter weights can be stored in a look-up table. A range of composite parameters of interest is selected so as to calculate a particular blood constituent, such as blood glucose. This multi-LED system can be used on the back of a watch (FIG. 6) as a non-invasive glucose sensor. In various embodiments, the parameters are trained with invasively-measured glucose over a general population of interest; the highest correlation with invasively-measured glucose over a specific population matching a patient of interest; or the lowest error in the measurement of glucose, for example. The neural network derives glucose estimates based on the average glucose across a population of individuals according to the measured parameters. The population-based glucose estimate can also be refined by receiving an individually-calibrated glucose from a blood glucose sensor and noninvasive sensor estimate.

In yet another embodiment, glucose is detected by high-frequency radio waves around the 65 GHz range, such as those generated by ultrawide band or 5G transceivers. These waves are large enough to allow penetration through the tissue, yet simultaneously small enough to provide sufficient resolution of the blood regions inside the tissue and the blood glucose concentration can be measured at the capillary level instead at the IF. The RF waves pass through one side of a finger or ear lobe and sensed on the other side of the finger or lobe in one implementation. In another implementation, the RF waves are reflected or back-scattered from the wrist or mouth using a tooth mounted transceiver aimed at the mucosa, for example.

In other embodiments, a non-invasive sensor from a wearable device, a mobile phone or watch can act as a spectrometer which generates a spectrum of light in the visible and near infrared regions. The light is first modulated to provide light signals which can be processed to minimize background noise resulting from ambient light and other stray signals and directed to the source of the analyte, i.e. glucose, to be measured. The glucose source is blood within the tissue of an ear lobe, finger, or wrist region suitable for watch-based monitoring. The light may be transmitted through the ear lobe or may be caused to impinge on the skin surface of the tissue (such as a patient's wrist) at an angle where it is absorbed by tissue material near the surface and reflected as diffuse radiation. In either case, the light is spectrally-modified as a result of infrared absorption by the blood and tissue components, including glucose. The light can be directly beam/retrieved from the skin or can be communicated using fiber optics, among others. In the embodiment utilizing diffuse reflectance, a near infrared bandwidth in the range of 1800 to 3400 nm is preferred. Glucose is strongly absorbing in this range but, because of the similar high absorbance by water in this region, transmissive measurements are not practical. Human skin layers act as a natural filter that allow smaller glucose molecules to move to the surface, but restrict movement thereto of the larger protein molecules. Therefore, reflective skin surface measurements are less subject to protein interference than are transmissive measurements. Furthermore, a correlation between skin surface glucose and serum glucose has been established and direct measurement of the former can be converted into the latter. The intensities of the reflected light are detected by photosensor(s). For the infrared bandwidth indicated above, a lead sulfide photodetector can be used, but other types also work. The photosensors convert the measured light into signals representative of the light intensities and used to calculate the actual glucose concentration. When utilizing reflective measurements at longer wavelengths (in the range of 2700 to 3400 nm for glucose analysis, sensitivity may be substantially enhanced because of the stronger absorbance by glucose in this range.

In one embodiment an LED is used as a light source with a CMOS camera as the detector. A grating similar to compact disk (CD) grating serves as the dispersive placed about 50 mm away from the LED, and slightly tilted at an incident angle of α=5°. The LED light passes through a pinhole with a diameter around 1 mm in front of the LED. The grating tracks are aligned normal to the incident light, and the light is then diffracted from the CD grating on the camera to detect glucose utilizing a bienzymatic cascade assay. Glucose detection can be based on a solution containing 2,2'-azino-bis(3-ethylbenz-thiazoline-6-sulfonic acid) (ABTS), horseradish peroxidase (HRP), and glucose oxidase (GOx). In this assay, glucose is catalytically converted (by GOx) into hydrogen peroxide, which in turn converts ABTS by HRP into its oxidized form (blue). For example, in the presence of 1 mM glucose, ABTS changes the color from colorless to blue and the absorption band appears at about 420 and 650 nm. Fabry-Perot interferometers configurations can also be used.

Capillary blood glucose levels at the fingertip correlate well with systemic arterial blood glucose levels. During times of blood glucose stability, identical glucose levels were demonstrated from alternate sites (e.g., forearm) as compared with finger-tip samples. However, at times of rapid change, mainly due to blood flow variability, levels from alternate sites differ considerably. Capillary blood glucose measured from the forearm is lower than fingertip values at times of rapid increases (>2 mg/dL/min) in systemic blood and higher during rapid decreases. The processor compensates accordingly for blood flow variability based on optical detection of blood flow as applied to a lookup table, a best-fit model, or a learning machine, among others. Further, the affections to the optical signals caused by the heartbeats may be obviated and samplings are not conducted at the peak of the heartbeats.

Embodiments of the glucose sensor can also monitor biomarkers of glycemic control. Hemoglobin A1c (A1C) is the best biomarker indicator of glycemic control over the past 2-3 months due to strong data predicting complications. Hemoglobin A1c refers to the non-enzymatic addition of glucose to the N-terminal valine of the hemoglobin beta chain. Assays are based upon charge and structural differences between hemoglobin molecules. Therefore, variants in hemoglobin molecules may lead to analytic interferences. It should be noted that some homozygous hemoglobin variants (HbC or HbD, or sickle cell disease) also alter erythrocyte life span and therefore, even if the assay does not show analytic interference, other methods of monitoring glycemia should be utilized, as HbA1c will be falsely low. Fructosamine refers to a family of glycated serum proteins and this family is comprised primarily of albumen and to a lesser extent, globulins, and to an even lesser extent, other circulating serum proteins. No product exists for home use that measures serum fructosamine. The largest constituent of fructosamine is glycated albumin. Several investigators and companies are developing portable assays for glycated albumin to assess overall control during periods of rapidly changing glucose levels. In these situations, an A1C test may change too slowly to capture a sudden increase or decrease in mean glycemia. The aforementioned biomarkers for measuring glycemic control, (A1C, fructosamine, and glycated albumin) only reflect mean levels of glycemia. These measures can fail to portray hyperglycemic excursions if they are balanced by hypoglycemic excursions. Plasma 1,5-anhydroglucitol (1,5-AG) is a naturally occurring dietary monosaccharide, with a structure similar to that of glucose. The 1,5-AG levels respond sensitively and rapidly to rises in serum glucose and a fall in the serum level of this analyte can indicate transient elevations of serum glucose occurring over as short a period as a few days. Measurement of 1,5-AG can be useful in assessing the prior 1-2 weeks for: 1) the degree of postprandial hyperglycemia; and 2) the mean short-term level of glycemia. This assay might prove useful in assessing the extent of glycemic variability that is present in an individual with a close-to-normal A1C level, but who is suspected to be alternating between frequent periods of hyperglycemia and hypoglycemia. In such a patient, the 1,5-AG level would be low, which would indicate frequent periods of hyperglycemia, whereas in a patient with little glycemic variability, the 1,5-AG levels would not be particularly depressed because of a lack of frequent hyperglycemic periods.

In another embodiment, the glucose concentration can be detected using a wearable eyeglass or an AV/VR goggle providing LEDs as laser sources. The user's eye is automatically scanned using a dual source of polarized radiation, each transmitting at a different wavelength at one side of the cornea of the patient. A sensor located at the other side of the cornea detects the optical rotation of the radiation that passed through the cornea. The level of glucose in the bloodstream of the patient is a function of the amount of the optical rotation of the radiation detected at the other side of the cornea of the patient. The system performs the following: scan eyes using a dual source of polarized radiation, each transmitting at a different wavelength at one side of the cornea; at the other side of the cornea, detecting the optical rotation of the radiation that passed through the cornea; determine the level of glucose in the bloodstream of the patient as a function of the amount of the optical rotation of the radiation detected at the other side of the cornea of the patient.

The result is transmitted to a remote receiver to provide non-invasive glucose determinations with high specificity and reliability. The outputs of all LEDs are individually calibrated against the gold standard blood-based glucose level, and the output of a neural network finalizing the glucose level determination is also calibrated against the blood-based glucose level. In addition, the neural work also compensates for glucose level based on temporal activities such as exercise, food type, emotion level as detected through bioimpedance readings, among others. For example, if the user is dehydrated, the neural network learns over time to increase the glucose determination based on a deterministic or non-deterministic compensation factor. The eyewear glucose determination can be singly or can be supplemented with a bioimpedance sensor electrically coupled to the user as detailed below.

In another embodiment, a bioimpedance sensor can be operated at a high frequency (ZHF) and a low frequency (ZLF) for detecting glucose level. High frequency HF is chosen from the range from 200 kHz to 2 MHz; low frequency LF is chosen from the range from 20 kHz to 80 kHz. Electrical impedance of components of electrical impedance of body region tissues can be measured by radiating high-frequency oscillations and subsequent measuring the impedance by means of capacitive sensors. Impedance of a human body region is measured at time intervals chosen from the range from 1 sec to 10 min. ZHF is used to obtain the value of the volume of fluid in the tissues of the region. ZLF is used to obtain the value of the volume of extracellular fluid in the tissues. The increase in the metabolic component in the volume of extracellular fluid is determined by the increase of the volume of all of the fluid in comparison with the previous measurement, determining the increase in the volume of extracellular fluid in comparison with the previous measurement and subsequently calculating the difference between the increases in the volume of all of the fluid and the volume of extracellular fluid. The glucose concentration is determined by adding the amount of increase in the glucose concentration and the value of the glucose concentration determined at the previous measuring stage. Thus, knowing the initial value of glucose concentration in human blood G0 and periodically taking measurements of impedance of the human body region at high and low frequencies—ZHF(tk) and ZLF(tk), the current value of glucose concentration in human blood is determined. The bioimpedance sensor characterizes changes in volumes of water spaces in human tissues, and the current value of glucose concentration in human blood, including individual physiological features of human being and moments of food intake. The measurements are periodically made and confirmed by the gold standard invasive method such as CGM or blood test strips with blood samples taken every 15 minutes. The results of the discrete measurements were recorded, and curves showing the relation of time t versus blood glucose concentration G can be generated.

In a further embodiment, a combination of sensors along with machine learning is used to accurately and non-invasively detect glucose. In one embodiment, optical sensors such as LEDs used to detect blood flow under the skin is combined with the bioimpedance sensor to improve glucose determination. The outputs of all sensors are individually calibrated against the gold standard blood-based glucose level, and the output of the neural network finalizing the glucose level determination is also calibrated against the blood-based glucose level. In addition, the neural work also compensates for glucose level based on temporal activities such as exercise, food type, emotion level as detected through bioimpedance readings, among others. For example, if the user recently jogged 4 miles, the neural network learns over time to deduct from the glucose determination based on a deterministic or non-deterministic compensation factor.

In another embodiment, the combination of sensors along with machine learning is used to accurately and non-invasively detect glucose, and where a LED spectrometer on the wrist or ear lobe or any suitable body location is combined with the bioimpedance sensor to improve glucose determination. SpO2 or ECG based heart rate sensor(s) can be used to detect activities and calorie consumption. The outputs of all sensors are individually calibrated against the gold standard blood-based glucose level, and the output of the neural network finalizing the glucose level determination is also calibrated against the blood-based glucose level. In addition, the neural work also compensates for glucose level based on temporal activities such as exercise, food type, emotion level as detected through bioimpedance readings, among others. For example, if the user recently jogged 4 miles, the neural network learns over time to deduct from the glucose determination based on a deterministic or non-deterministic compensation factor. Moreover, if the user just ate a food item, the learning machine or neural network projects the digestive time from eating to glucose level and generates the glucose estimation after training with blood-based glucose level from invasive devices. Initially, the user received a predetermined nutritional load consisting of different food products. The blood glucose concentration is measured from the beginning of the meal until the food-related growth of glucose concentration stopped.

The sensor and insulin supply can be combined to form an artificial pancreas. This can be user operated or computer controlled. For user control of the CGM and insulin injection, one embodiment provides tiered recommendations that are based upon the meter glucose and sensor trend where patients increase or decrease the meal+correction bolus by 10-20% based upon the rate of change and provided specific instructions for responding to alarms. Other methods recommended adjustment of only the correction insulin dose by the amount needed to cover a glucose level that is incrementally higher or lower than the current glucose, based upon the trend. Another method adjusts boluses pre-meal and at least 4 hours post-meal in 0.5 unit increments based upon the trend arrow and the patient's sensitivity. A computer-controlled embodiment provides an artificial pancreas with 1) an automatic and continuous glucose monitor; 2) an implanted continuous insulin delivery system; 3) a control processor to link the insulin delivery rate to the glucose level; and 4) a radio to send the glucose level to the body surface for continuous display onto a monitor. The neural network predictive algorithm enhances sensor accuracy and reduces issues such as lag time, inadequate onset and offset of currently available rapid acting insulin analogs, meal challenges, and changes in insulin sensitivity due to circadian rhythms, exercise, menstrual cycles, and intercurrent illness. The system improves glucose control without increasing the complexity of decision-making on the part of the patient. The system can work with open-source software, such as Open Artificial Pancreas System, and Loop, for example.

The system can use single hormone (rapid acting insulin only) or dual hormone (both fast-acting insulin analog and glucagon to imitate normal physiology) as directed by the sensor/processor to provide reduced hypoglycemic events and time in hypoglycemia, as well as better overall mean glucose and glycemic variability. An adaptive meal-priming insulin bolus automatically adjusts the size of breakfast, lunch, and dinner doses by delivering 75% of the average prandial insulin provided for previous meals at that time of day improved glucose control compared to no meal announcement during dual hormone system.

Direct connectivity of blood glucose or CGM levels to cell phones or other devices improves data integrity and may also simplify the assimilation of glucose levels with other data such as insulin use, carbohydrate intake and activity levels for the purpose of facilitating insulin dose adjustments in real time or retrospectively. In one embodiment, smartphone software serves as a bolus calculator, enables self-titration of insulin, and transmits data to health care providers. The system provides immediate personalized feedback to the patient based upon glucose levels, tailored text messages, and access to certified diabetes educators in real time. A patient portal also allows for integration of data from multiple sources including third party nutrition and exercise apps. Providers can easily access dashboard reports for population and telehealth programs. The system can provide patient coaching as well as provider clinical decision support. Patients view data via their mobile device through a web portal and receive automated text messaging responses that are tailored to the data. Diabetes educators or other providers may view the data and send supplemental feedback as well.

One embodiment to guide the user on healthy food determines a glycemic index (GI), a value assigned to foods based on how slowly or how quickly those foods cause increases in blood glucose levels. Blood glucose levels above normal are toxic and can cause blindness, kidney failure, or increase cardiovascular risk. Foods low on the GI scale tend to release glucose slowly and steadily. Foods high on the glycemic index release glucose rapidly. Low GI foods tend to foster weight loss, while foods high on the GI scale help with energy recovery after exercise, or to offset hypo- (or insufficient) glycemia. Long-distance runners would tend to favor foods high on the glycemic index, while people with pre- or full-blown diabetes would need to concentrate on low GI foods as they typically can't produce sufficient quantities of insulin—which helps process blood sugar—which means they are likely to have an excess of blood glucose. The slow and steady release of glucose in low-glycemic foods is helpful in keeping blood glucose under control. A list of the glycemic index and glycemic load for more than 1,000 foods can be found in Table 1 of the article "International tables of glycemic index and glycemic load values: 2008" by Fiona S. Atkinson, Kaye Foster-Powell, and Jennie C. Brand-Miller in the December 2008 issue of Diabetes Care, Vol. 31, number 12, pages 2281-2283, the content of which is incorporated by reference. In one embodiment for GI estimation for specific food products, as well as their combination consumed during a meal, i.e., mixed food load GI estimation. One embodiment determines carbohydrate content (in grams) of the consumed food, and, based thereon, a proportion of carbohydrate content in a given food product in the total nutritional load is determined. Thereafter, the glycemic index of each food product is multiplied by its specific carbohydrate content proportion, with the results are summed up to yield the total glycemic index of the nutritional load GI.

One embodiment estimates GI based on Jennie Brand-Miller et al., "The glucose revolution: the authoritative guide to the glycemic index, the groundbreaking medical discovery" by Marlow & Company, New York, 1999, p. 33, and Jennie Brand-Miller et al., "Moreover, Glycemic index, postprandial glycemia, and the shape of the curve in healthy subjects: analysis of a database of more than 1000 foods", Am J Clin Nutr 2009; 89:97-105, the contents of which are incorporated by reference. A neural network is applied to learn the relationship of glucose and GI using reference glucose from blood glucose testing, noninvasive glucose sensor output, and GI, and after training, the neural network is used to estimate glucose and glycemic index (GI).

To collect training data, in one implementation, personalized food selection for glucose control is done after characterizing the body's reaction to specific food. This is done in 3 cycles. In the first cycle, characterization is done where the user eats 7 different meals which are all designed to contain the exact same amount of the macronutrients (carbohydrates, proteins, and fat). The day before user eats a standardized meal, no any strenuous physical activity producing sweat is performed between noon the day before the meal and 2.5 hours after the consuming the meal. The user should fast for 10-15 hours between dinner the night before and eating the standardized meal (eg. Eat dinner at 6:30 pm, fast for 10-15 hours, eat standardized meal at 7:30 am=13 hour fast). Preferably the day of the standardized meal: eat the standardized meals in the morning, within 30 minutes of waking up; consume the meal in a time span of 10 minutes without drinking a caffeinated beverage on the mornings of the standardized meals. The user should refrain from eating or drinking caffeine or other foods for a minimum of 2.5 hours after the meal (water is fine).

In one implementation, the Standardized Meals are consume in order of the following: #1—Berries—Strawberries 160 gr, Blueberries 100 gr, Raspberries 170 gr; #2—Grape meal—Grape, Red or Green (European Type, such as Thompson Seedless), Adherent Skin, Raw 275 gr; #3—Rice meal—jasmine, cooked, from frozen 155 gr; #4—Bread meal, country white 2.5 slices; #5—Pasta Dry, Enriched 70 gr; #6—Potato meal—Shredded Hash Brown, Frozen 300 gr; #7—Beans—black beans, cuban style, canned 1 can. GI for the food is looked up in a table such as Table 1 of the Atkinson publication, or data from Jennie Brand-Miller publication. GI characterizes foods by using the incremental area under the glycemic response curve relative to a similar amount of oral glucose. In this embodiment, GI characterizes foods by using the incremental area under the glycemic response curve relative to a similar amount of oral glucose. Measurement of blood glucose concentration starts when food intake begins. The measurements are performed continuously or over certain periods of time, which provides a sufficient reliably of evaluating changes in blood glucose concentration over time t. Due to food intake, blood glucose concentration of the consumer reaches a maximum value after a predetermined duration (typically 2.5 hrs) and thereafter, the glucose concentration declines and the measurement is stopped. The shape of the curve in healthy individuals and the GI of individual foods correlates strongly with the incremental and actual peak, incremental and actual glucose concentration at 60 min, and maximum amplitude of glucose excursion.

Another embodiment extends the above cycle into cycles 2 and 3 to identify personalized diet to reduce diabetic problems. For cycle #2 the food that had the strongest glucose response from cycle #1 and the selected food is tested against 3 different supplements (to try in three different days): 1—Boiled egg whites as a source of protein; 2—Fresh cream as a source of fat; and 3—Pea fiber powder as a source of fiber, for example. Cycle 2 tests if any of the supplements would help in attenuating the glucose peak. For cycle #3 the selected "optimal" diet is then tested for glucose efficacy. For the embodiment, an exemplary process to treat an insulin condition includes:

characterizing body glucose responses to a plurality of standardized meals, each containing a predetermined number of macronutrients;

selecting the standardized meal with a glucose peak response and further testing the selected standardized meal against supplements of protein, fat, or fiber;

selecting the supplement best attenuating the glucose peak response for a predetermined diet;

testing the predetermined diet for glucose efficacy in a selected glucose range.

In another embodiment, an exemplary process to treat an insulin condition includes:

characterizing body glucose responses to a plurality of standardized conditions;

detecting a glucose level and when the level is outside of a predetermined boundary, applying one of the standardized conditions to bring the glucose level within the predetermined boundary.

In yet another embodiment, an exemplary process to treat an insulin condition without medication includes:

characterizing body glucose responses to a plurality of standardized conditions;

characterizing body glucose responses to a plurality of standardized meals, each containing a predetermined number of macronutrients;

selecting the standardized meal with a glucose peak response and further testing the selected standardized meal against supplements of protein, fat, or fiber;

selecting the supplement best attenuating the glucose peak response for a predetermined diet;

testing the predetermined diet for glucose efficacy in a selected glucose range;

detecting a glucose level and when the level is outside of a predetermined boundary, applying one of the standardized conditions to bring the glucose level within the predetermined boundary.

The neural network is trained on temporal and/or spatial relationships that affect glucose level. In one embodiment, calibrated glucose data from blood-based glucose monitoring device is added to the data to train the non-invasive glucose determination logic, and such data is captured over time (temporal) and over related markers (spatial). The neural network is then able to accurately estimate glucose level based on the non-invasive sensor output and the markers that are captured by sensors such as accelerometers to detect exercise activity, cameras to detect food quantity/quality, and locality activity of life data from mobile devices (time, temperature), among others. Exemplary markers include:

Carbohydrate quantity—Of all the three sources of energy from food (carbohydrates, protein, and fat), carbohydrates affect blood glucose the most. Accurately counting carbs is difficult, and getting the number wrong can dramatically affect blood glucose. The type of carbohydrate also matters—higher glycemic index carbs tend to spike blood glucose more rapidly.

Carbohydrate type—veggies (especially greens), nuts, seeds, chia pudding, berries—tend to have 50%-80% of the carbs from fiber and are very low in sugar. Foods with a high-fiber-to-total-carbs ratio have a lower impact on blood glucose vs. foods with the same amount of total carbs but no fiber. In addition, the more grams of carbs that come from sugar, the higher the impact on blood glucose—even if total carbs are the same. Last, food form also matters—liquid carbs will usually increase blood glucose more quickly than solid carbs, even if the overall carbs are equal.

Fatty foods tend to make people with diabetes more insulin resistant, meaning more insulin is often needed to cover the same amount of food relative to a similar meal without the fat. The hardest meals are those with lots of fat and lots of carbs. On a pump, using temporary basals or extended boluses (square and dual-wave) can help cover the slow, steady BG rise from high-fat meals.

Protein—a large protein-only meal with very few carbs (e.g., salad with chicken) may cause a small rise in blood glucose (~20-50 mg/dl). The consumption of a carb-free, protein-only meal requires insulin to cover the slow rise in BG (usually an equivalent of about 10-15 grams of carbs). Pure protein powders (with no carbs) can also increase blood glucose.

Caffeine increases insulin resistance and stimulates the release of adrenaline. A large cup of coffee may cause a 20-40 mg/dl rise in blood glucose. Tea also has a small glucose effect.

Alcohol Normally, the liver releases glucose to maintain blood sugar levels. But when alcohol is consumed, the liver is busy breaking the alcohol down, and it reduces its output of glucose into the bloodstream. This can lead to a drop in blood sugar levels if the alcohol was consumed on an empty stomach. However, alcoholic drinks with carbohydrate-rich mixers (e.g., orange juice) can also raise blood sugar. When drinking alcohol, make sure you check your blood glucose often and that someone responsible nearby knows you have diabetes.

Meal-timing—eating a large late-night dinner often results in high overnight blood sugars (over 180 mg/dl), especially if it's a meal high in carbs and fat. A lighter, earlier dinner seems to improve the overnight numbers.

Dehydration—in a randomized, controlled 2001 study, dehydration raises blood glucose levels for those in a fasted state (Burge et al., Metabolism). The New York Times also reported that dehydration increases levels of the hormone vasopressin, which pushes the liver to produce blood sugar (Anahad O'Connor, January 16).

Personal microbiome—Gut bacteria ("microbiome") can affect blood glucose levels and insulin sensitivity. For example, artificial sweeteners may negatively affect the microbiome and glucose responses (Nature 2014).

Medication dose and Medication timing can also be critical. For instance, taking rapid-acting insulin (Humalog, Novolog, Apidra) 20 minutes before a meal can lead to a lower spike in glucose vs. taking it at the start of the meal or after the meal has concluded. The timing of many type 2 diabetes medications matters too—some can consistently be taken at any time of day (e.g., Januvia, Victoza), while others are most optimally taken at meals (e.g., metformin).

Steroids like prednisone can significantly increase blood glucose levels, in part by telling the liver to increase glucose production. Once prednisone is stopped, blood glucose levels usually return to normal fairly quickly.

Niacin (Vitamin B3)—Studies show niacin does increase blood glucose levels modestly. Niacin is typically prescribed to improve blood lipid levels, including HDL cholesterol and triglycerides (i.e., to improve heart health).

Light exercise activity can have a glucose-lowering effect and light exercise can act as a "dose" when blood glucose is high or trending high, especially after meals.

High intensity & moderate exercise—High-intensity exercise, such as sprinting or weight lifting, can sometimes raise blood glucose. This stems from the adrenaline response, which tells the body to release stored glucose. Often, high-intensity exercise can also drop blood glucose very rapidly (2-3 mg/dl per minute), especially if insulin was taken prior to exercise.

Level of fitness/training can affect glucose—someone starting a new activity (or starting any exercise) may see profound blood glucose drops initially, which may get smaller over time as level of fitness improves.

Time of day can affect glucose. Depending on when the patient is insulin resistant, the glucose may vary, and understanding more about morning sensitivity in exercise is especially possible through CGM.

Food & insulin timing can affect glucose. Eating too close to starting activity can lead to a low BG during activity (food has not been absorbed) followed by a high BG afterwards (food hits the bloodstream once exercise ends and digestion restarts).

Sleep—More insulin may be needed on days following less than seven hours of sleep and glucose is more variable without sufficient sleep and studies have found that not getting enough sleep leads to higher blood sugars, insulin resistance, weight gain, increased food intake, and more carb cravings.

Stress and illness can cause the body to release adrenaline (epinephrine), glucagon, growth hormone, and cortisol. As a result, more glucose is released from the liver (glucagon, adrenaline) and the body can become less sensitive to insulin (growth hormone, cortisol).

Recent hypoglycemia or "hypoglycemia begets hypoglycemia"—recent hypoglycemia impairs the body's defense mechanisms against lows. When another low comes up, it's harder to recognize the symptoms and/or the body has a harder time avoiding it.

During-sleep blood sugars—overnight blood sugars can impact on next-day time-in-range—if patient spends all night high—especially over 180 mg/dl, s/he is more likely to fight high blood sugars the whole next day. Conversely, if glucose of most of the night in range, the next day gets off to a far better start.

"Dawn phenomenon" refers to the body's daily production of hormones around 4:00-5:00 AM. During this time, the body makes less insulin and produces more glucagon, which raises blood glucose. User may need to time the dose to cover this early morning rise in glucose.

Intramuscular insulin delivery—Injecting or pumping insulin into a muscular/low-body-fat area can increase the risk of hypoglycemia—especially if it happens before activity.

Allergies—High glucose levels may occur when they have allergies, possibly due to the stress hormone cortisol.

High BG level (glucotoxicity)—High blood sugars can lead to a state known as "glucotoxicity," which can actually cause insulin resistance on its own.

Periods (menstruation)—Many women report having higher blood sugar levels a few days prior to their period starting, but some women notice a sharp drop in sugar levels.

Puberty—High levels of hormones secreted during puberty—growth hormone, testosterone, estrogen, cortisol—can increase insulin resistance. Adolescents with diabetes may need as much as 30%-50% more insulin than adults to keep their numbers within range.

Celiac disease—Untreated celiac, leading to a damaged small intestine, can increase the risk of hypoglycemia because the small intestine may no longer be able to absorb nutrients properly. Beyond Celiac also notes that untreated celiac may contribute to "irregular blood glucose levels."

Smoking—Studies suggest that smoking can increase insulin resistance, and people with diabetes who smoke are more likely than non-smokers to have trouble with insulin dosing and managing their diabetes. Smokers also have higher risks for serious complications.

Outside Temperature—Cold exposure can improve insulin sensitivity in type 2 diabetes. Some people with diabetes also report that sitting in the sun drops their blood glucose as the blood vessel dilation from heat might be responsible (similar to the effect in a hot shower or hot tub).

Sunburn stresses the body and can increase blood glucose. This is related to the previous factor on "stress/illness."

Altitude can increase insulin resistance and users may need about 20-30% more basal insulin. However, if users go to a high altitude place to do activity (e.g., skiing), less insulin may be needed.

Some embodiments track cardiovascular sensor data with glucose data to provide enhanced glucose determination. IGT may occur with almost as high a frequency as diabetes and is accompanied by an increased frequency of CVD and its risk factors. Estimates indicate that >12.0% of all ECG-indicated CHD in the population occurs in individuals with IGT and NIDDM. Further, heart rate variability (HRV) is a noninvasive measure of the autonomic nervous system, and its dynamic physiological nature provides an alternative means of blood glucose monitoring. In embodiments, Low-frequency (LF) power, high-frequency (HF) power, and total power (TP) of HRV were negatively associated with BGL in participants with DM. Additionally, the ratio of LF to HF was positively correlated with BGL. Duration of DM was also associated with multiple HRV parameters, with negative associations to both LF and HF parameters as well as TP. The neural network automatically learns links between specific HRV variables and BGL. Further, glycemia under 3 mmol/l and over 19 mmol/l is associated with significantly longer QTc interval compare to other blood glucose levels. A moderate correlation was found between a daily insulin dose and QTc duration. Glycemia under 3 mmol/l and over 19 mmol/l can prolong QT interval and, therefore, raise the risk of cardiovascular death in patients with type 1 DM.

These relationships are also learned by the neural network in the processes shown in FIGS. 2A-2G that analyze glucose and heart data for health issues. The heart data can include ECG, heart rate, or blood pressure. Both hypertension and diabetes may have some underlying causes in common, and they share some risk factors. They also contribute to a worsening of each other's symptoms. The ways of managing both conditions also overlap. Insulin is the hormone that enables the body to process glucose from food and use it as energy. As a result of insulin problems, glucose cannot enter the cells to provide energy, and it accumulates in the bloodstream instead. As blood with high glucose levels travels through the body, it can cause widespread damage, including to the blood vessels and kidneys. These organs play a key role in maintaining healthy blood pressure. If they experience damage, blood pressure can rise, increasing the risk of further harm and complications. High glucose levels in the blood can increase blood pressure as the blood vessels lose their ability to stretch; the fluid in the body increases, especially if diabetes is already affecting the kidneys; and insulin resistance may involve processes that increase the risk of hypertension. Controlling blood sugar levels and blood pressure in FIGS. 2A-2G can help prevent complications.

Figure 3A:
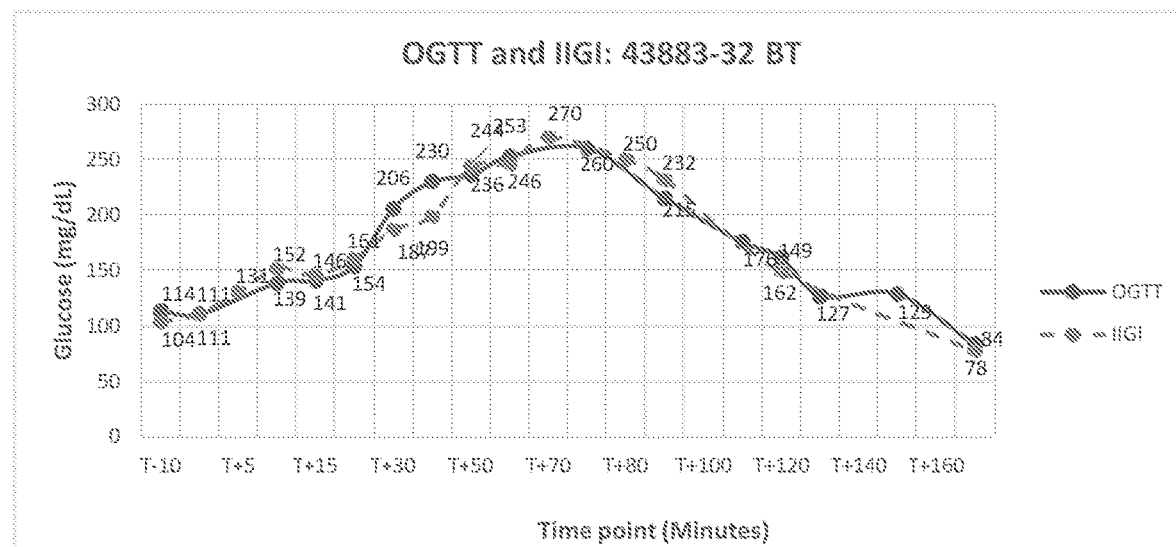
FIGS. 3A-3C show exemplary glucose charts from OGTT initial characterization of the user, a comparison of non-invasive glucose sensor using bioimpedance sensors with a CGM.
Figure 3B:
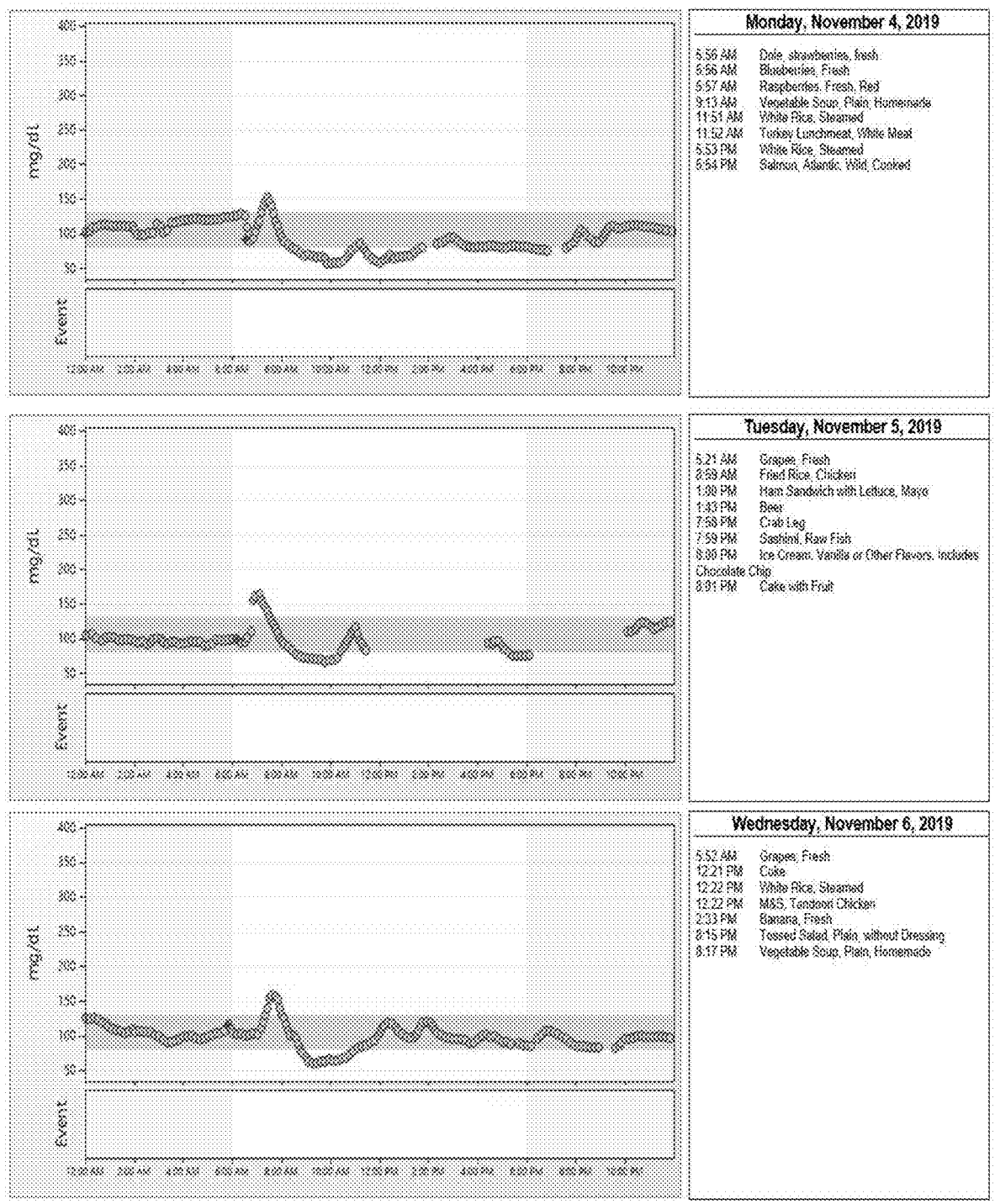
Figure 3C:
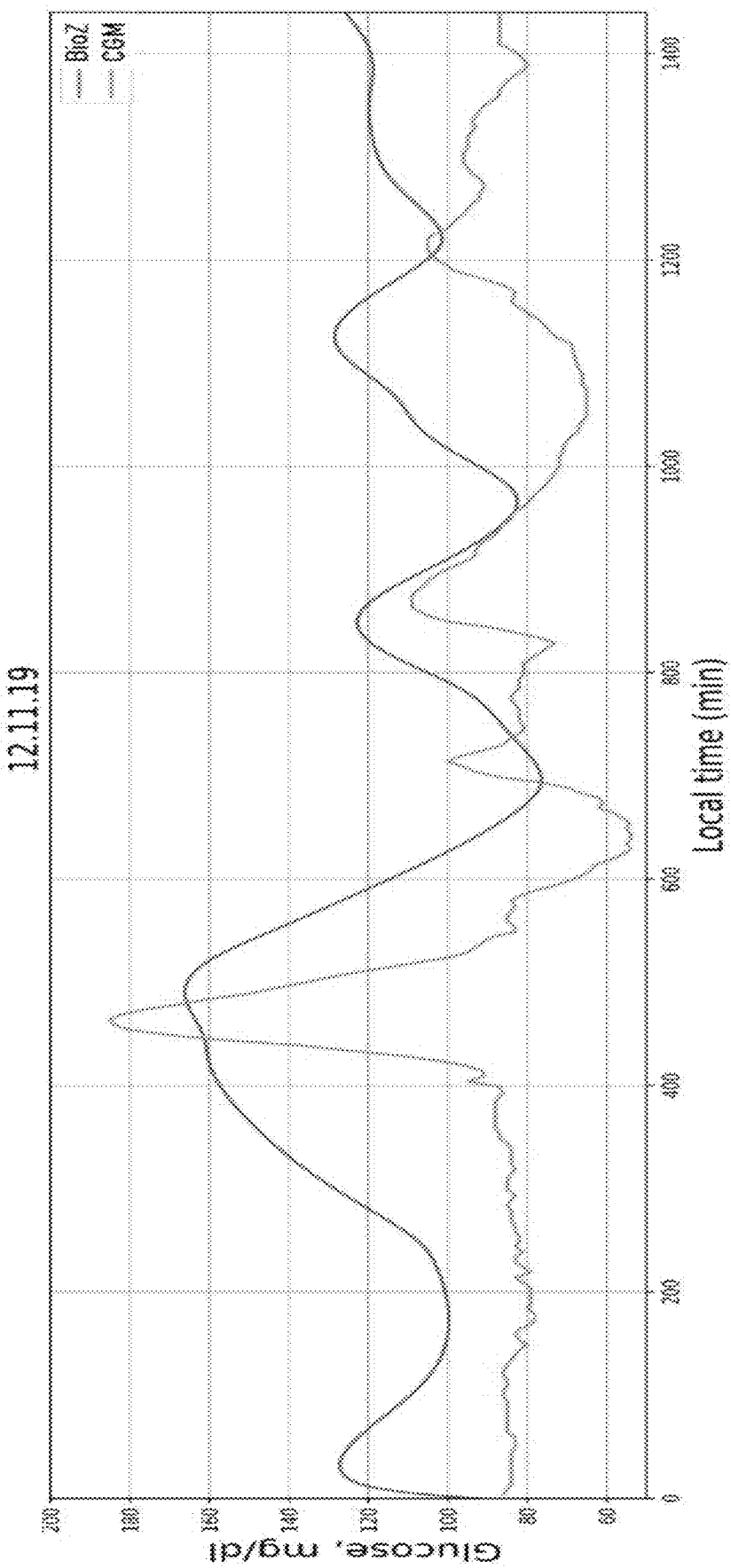
Figure 3D:
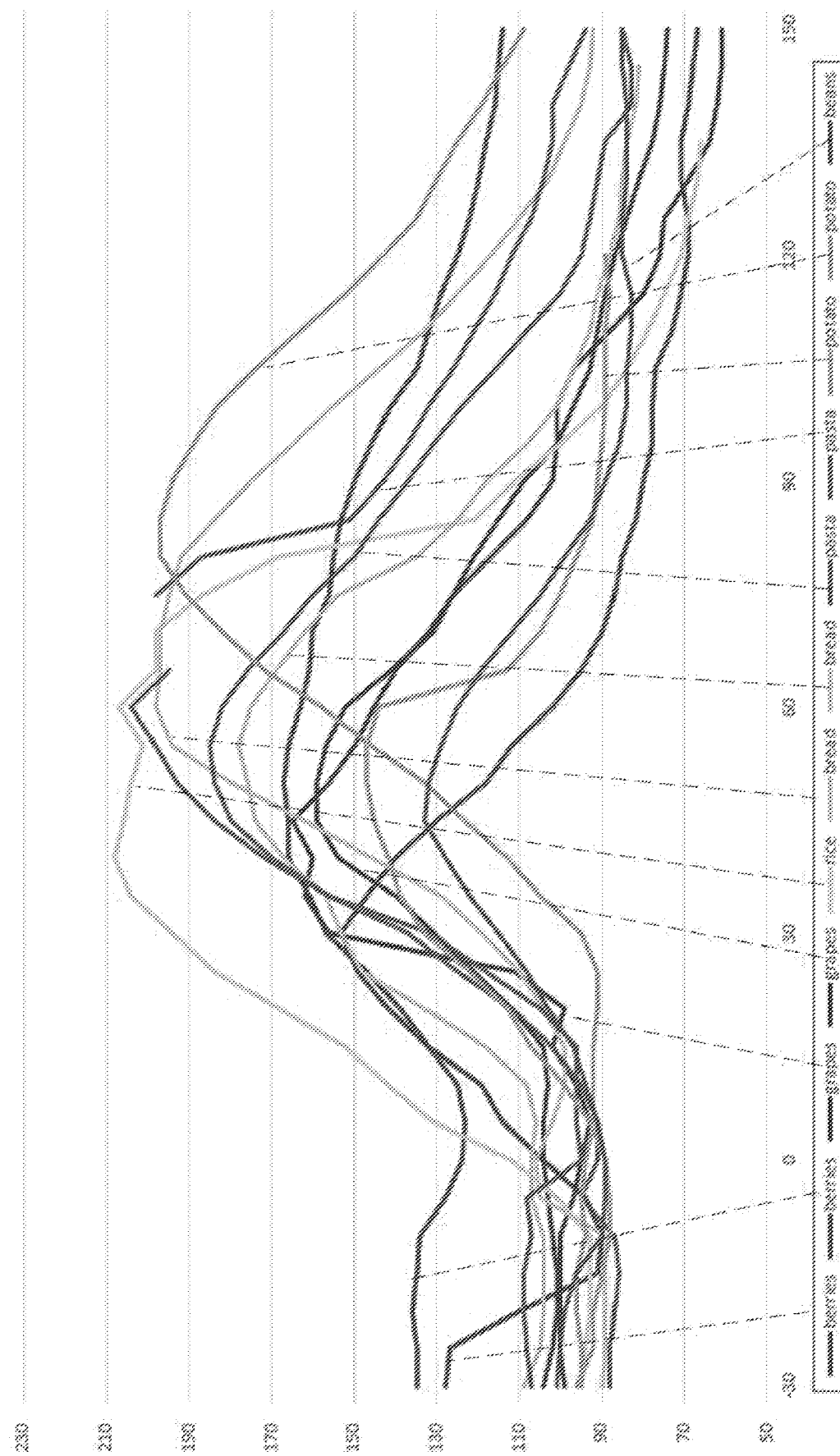
FIG. 3D shows exemplary food glucose response curves for various food items.
Figure 3E:
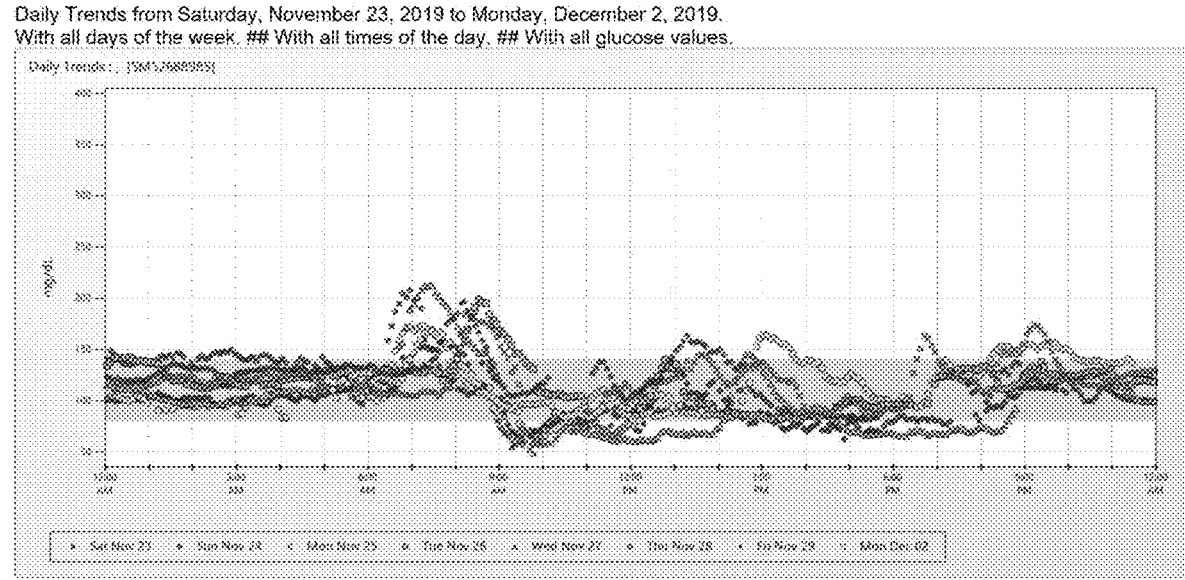
FIG. 3E shows daily glucose trends.
Figure 3F:
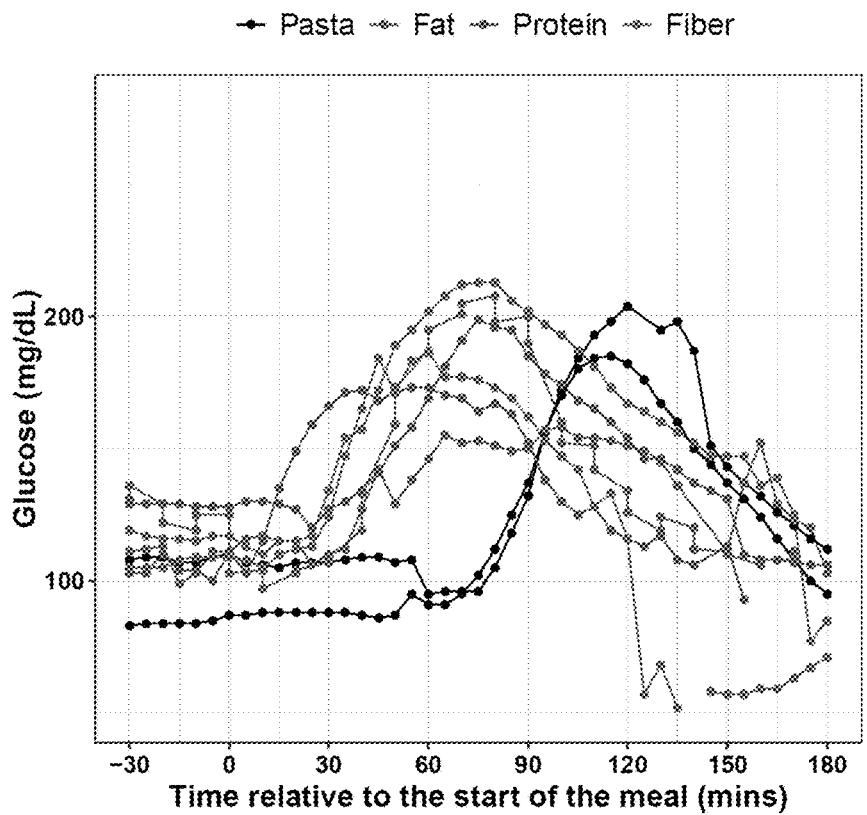
FIG. 3F shows the effect of various food combinations (fat, protein, fiber) with pasta on glucose.

FIGS. 3A-3C show exemplary glucose charts from OGTT initial characterization of the user, a non-invasive sensor using bioimpedance sensors, and from a CGM (Dexcom 4), FIG. 3D shows exemplary food glucose response curves for various food items, FIG. 3E shows daily glucose trends, and FIG. 3F shows the effect of various food combinations (fat, protein, fiber) with pasta on glucose.

FIG. 3A shows an exemplary result from the oral glucose tolerance test (OGTT) and a corresponding isoglycemic intravenous glucose infusion (IIGI) study. The OGTT and IGI both increase blood sugar, but the OGTT tests a sugar solution drank by the user, versus during the IIGI sugar is injected directed with the IV to analyze the role of the gut hormones secreted during the OGTT, which is completely by-passed during the IIGI. FIG. 3B shows exemplary CGM outputs of a Dexcom 4 with food intake, while FIG. 3C shows an exemplary bioimpedance estimation of glucose level v. CGM output. The user receives a dose of oral glucose (the dose depends upon the length of the test). Blood samples are taken up to four times at different time points after consumption of the sugar to measure the blood glucose. The classic oral glucose tolerance test measures blood glucose levels five times over a period of three hours. Studies have shown that impaired glucose tolerance itself may be a risk factor for the development of heart disease, and impaired glucose tolerance may deserve treatment itself. FIG. 3D shows exemplary food glucose response curves for various food items. The user fasts for 10-12 hrs before digesting each food, and rests for 2.5 hrs before any significant activity is done to isolate the curve to the food digestion. As can be seen, high carb foods such as rice, bread causes higher spikes than berry and beans, for example.

FIG. 3E shows exemplary glucose trends. In general, glucose spiked in the morning due to a large test load of carbs consumed by the test subject. Approximately 2.5 hrs after eating the test load, the test subject ran for about 3 miles, and glucose level dropped to about 50 mg/dL. Then the subject ate lunch and performed daily activities, and the glucose level rises and falls. Approximately around 6-8 pm, the subject ate dinner, resulting in a rise of glucose, and the glucose level tended to stay constant around 100-150 mg/dL. This indicates that exercise in the evening should be done to bring down the glucose level.

FIG. 3F shows the impact of various food supplements (fiber, fat, and protein) on carb (pasta). In this particular chart, the effects were modest. The pea fiber had the least effect, while protein and fat both attenuated the peak of the glucose, indicating that the diet should include some fat and protein. For this patient, fruits and bean are better tolerated than the starts, and thus the subject should eat small portions of carbs. Based on the foregoing exemplary data, the coaching software recommends:

1—Maintain glucose level in the range of 70-140
2—Support good level of cholesterol and blood pressure with dietary intervention
3—Optimize nutrients from the diet.

In one exemplary system, the system builds a schedule of the user's activity as follows:

| Location | Time Start | Time End | Heart Rate | Glucose |
|---|---|---|---|---|
| Bed room | 10 pm | 6 am | 60-80 | 90-120 |
| Gym room | 6 am | 7 am | 90-120 | 100-50 |
| Bath room | 7 am | 7:30 am | 85-120 | 100-110 |
| Dining room | 7:30 am | 8:45 am | 80-901 | 120-200 |
| Home Office | 8:45 am | 11:30 am | 85-100 | 110-150 |
| ... | | | | |
| ... | | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

In one embodiment, learning machines such as data driven analyzers may be used to track the user habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

Based on the glucose level, activity data, and food data, the device can apply artificial intelligence (AI) to model the user body. The AI can be a learning system such as a statistical recognizer or a neural network (NN). The AI can estimate impact of a change in the user regimen (e.g., medication, food intake, physical activity) on the physiological system of the user. The NN receives data which is transformed into features for training and for live operation. The features include mathematical transformations of medication intake, carbohydrate intake, insulin level of the user, and glucose inventory of the user. The carbohydrate intake is determined based on the amount of carbohydrates ingested by the user that become the primary source of blood glucose for the user. The insulin level of the user is determined on a variety of factors including dosing, pancreatic production, and kinetics. The glucose inventory is determined based on the glucose stored in the liver, skeletal muscle, and fat tissues of the user. The processor may generate a modified model for the user through training with user data. In addition, population data from similar users may be used to generate a modified NN model for a particular user. The modified model can provide guidance to improve the patient's regimen and to gain a better understanding of how a particular user is being affected by a disease dynamic. The use of user data over an extended period of time allows the modification and improvements of the modified model as more data is collected for a particular user. The modified model may also be used even when limited/incomplete user data is received. One embodiment uses federated learning to improve global models in the cloud by leveraging on-device training on user data with differential privacy and protect privacy in federated learning. This is done to protect user privacy and comply with HIPPA regulations. The system uses differential privacy to add a further layer of protection and injects a small amount of noise into any raw data before it is fed into a local machine-learning model. The additional step makes it exceedingly difficult for malicious actors to reverse-engineer the original sensor files containing HIPPA data from the trained model.

Rather than aggregating the raw data to a centralized datacenter for training, federated learning leaves the raw data distributed on the device 102 or local clients 104 (mobile devices), and trains a shared model on the server by aggregating locally-computed updates. To optimize the gradient of a shared model by the distributed gradient updates on mobile devices, federated learning adopts stochastic gradient descent (SGD). SGD updates the gradient over extremely small subsets (mini-batch) of the whole dataset, which is a simple but widely-used gradient descent method, allowing the clients to train independently on their own datasets and selectively share small subsets of their models' key parameters to the centralized aggregator. Since SGD is easy to be parallelized as well as asynchronously executed, SSGD targets both HIPPA privacy and training loss. Specifically, while preserving client own privacy, the training loss can be reduced by sharing the models among clients, comparing to training solely on their own inputs. In another federated learning with the deep neural network based on iterative model averaging where the clients update the model locally with one-step SGD and then the server averages the resulting models with weights. In federated learning embodiment, each client sends a full model or a full model update back to the server in a typical round, or the computation of local updates can be done at the clients 102 or 104. However, it is impractical when the devices 102 are under severe computation resources constraint, various embodiments can use structured update or sketched update. In a structured update, the model directly learns an update from a restricted space parametrized using a smaller number of variables, e.g. either low-rank or a random mask. If using a sketched update, the model first learns a full model update and then compressed the update using a combination of quantization, random rotations, and subsampling before sending it to the server.

Though Federated Learning technique exploits a new decentralized deep learning architecture, it is built upon a central server for aggregating local updates. For non-central server implementations, a Bayesian-based distributed algorithm, each device 102 or 104 updates its belief by aggregating information from its one-hop neighbors to train a model that best fits the observations over the entire network. Furthermore, with blockchain, a Blockchain Federated Learning (BlockFL) can be used where the devices model update exchanged and verified by leveraging blockchain. BlockFL also works for a fully decentralized network, where machine learning model can be trained without any central coordination, even when some devices lack their own training data samples. More details on blockchain tamperproofing of systems are disclosed in U.S. Pat. No. 9,849,364 to the instant inventor, the content of which is incorporated by reference.

The AI model can estimate impact of a change in the user's regimen (e.g., medication, food intake, physical activity) on the physiological system of the user. The NN may update a base model for the user by bootstrapping from established knowledge of disease dynamics and factors and training with user generated data. The base model represents the minimal assumptions and parameters of a person's physiological system and the correlation of certain factors. How the factors interact and correlate is different for different users. The user data is used to adjust the basic model and generate a modified model for a particular user. The more user data is collected over time to train the NN, the more accurate the modified model is for the particular user. In addition, the collection of data from multiple similar patients from a population may be used to improve the NN model. The modified NN can provide guidance to improve the user regimen and to gain a better understanding of how a particular user is being affected by a disease dynamic. The use of user data over an extended period of time allows the modification and improvements of the modified NN model as more data is collected for a particular user. The modified NN model may also be used even when limited/incomplete user data is received as detailed above using federated learning with differential privacy.

The AI model is used to determine a plan to keep the glucose level to a predetermined range by instructing the user to eat a predetermined diet to keep the glucose level in range, or if the user eats too much or the body on its own increased the glucose level (as a natural reaction to a cold, a lack of sleep, or the onset of aging or a disease, among others), the device instructs the user to perform an exercise sequence that brings the glucose back into compliance as part of a closed-loop feedback using the bioimpedance sensor, among others. The embodiment also includes a script of coaching instructions that is selected based on the sensor output, and the coaching instructions can be rendered as audio to play on an earbud or headphone, for example.

The trained NN model can determine a rate of change in blood glucose level of the user over a time interval based on food intake, and blood glucose inventory to determine factors causing health variances from predetermined healthy levels (such as a glucose level range for healthy people) and develop a plurality of treatment recommendations to ameliorate negative effects of the blood glucose condition; automatically update the modified model when additional user data is received by the processor; and outputting the treatment recommendations. While non-medication solutions (such as reducing food intake and increasing physical activity at predetermined time) are preferred, one of recommendations can include dosing and timing of medication, or recommendations for user dietary behavior. Moreover, the timing/sequence of the medication, food intake, and physical activity can be optimized to control glucose with minimal medication intake. Another factor includes the timing of blood glucose measurement.

Blood Pressure Management

The above system can handle various other diseases. One such disease is cardiac related, such as high blood pressure. Blood pressure is normally lower at night while the user is sleeping. The blood pressure starts to rise a few hours before the user wakes up, and blood pressure continues to rise during the day, usually peaking in the middle of the afternoon. Then in the late afternoon and evening, the blood pressure begins dropping again.

The learning machine/AI detailed above can be used for blood pressure management. In this embodiment, NN features include mathematical transformations of medication intake, carbohydrate intake, ECG, and blood pressure (BP) of the user. Preferably the BP is cuffless using techniques such as Pulse Transit time or Arterial Tonometry, as detailed in U.S. Pat. No. 8,747,336 to the instant inventor, the content of which is incorporated by reference.

Since blood pressure and diabetes often are correlated, one embodiment monitors hybrid features include mathematical transformations of medication intake, heart rate, ECG, BP, carbohydrate intake, insulin level of the user, and glucose inventory of the user. The carbohydrate intake is determined based on the amount of carbohydrates ingested by the user that become the primary source of blood glucose for the user.

Users with high blood pressure should avoid caffeine right before activities that naturally increase the blood pressure, such as exercise, weightlifting or hard physical labor. To see if caffeine might be raising your blood pressure, check your blood pressure before drinking a cup of coffee or other caffeinated beverage and again 30 to 120 minutes afterward. If the blood pressure increases by about five to 10 points, the user may be sensitive to the blood pressure raising effects of caffeine.

When the sensors detect trending high blood pressure, the system can coach the user to perform the following and sensor feedback can guide the user until the BP reaches a target range. The exercises can include:

Relaxation exercise. Close eyes while sitting in a comfortable chair or lying down. Starting with toes, slowly clench one body part at a time. Hold for 5 seconds and relax. Keep going until the user has tightened and relaxed every part of the body.

Deep breathing. Sit in a chair with feet flat on the floor. Then close eyes and focus on breathing. Inhale slowly and deeply through the nose, filling up the lungs. Hold for a few seconds. Exhale slowly through the mouth. Let all the air out of the lungs like letting air out of a balloon, and repeat.

Music. Relaxing music can ease anxiety and depression and lower blood pressure. Find music that calms the user, then put on headphones and relax. Playlists of some of the user favorite stress-busting songs can be saved for playing as needed, and separate from the workout music.

Yoga. This can be done through an active video game or with biofeedback sensors that visually or verbally prompt the user.

Exercise. Certain exercises can help certain users relieve stress. For some people, running and hard-hitting sports push away their worries. For others, taking a quiet walk or a bike ride is calming.

Social Support Network

In one embodiment, the system provides a social environment using a social network similar to Facebook in which the participants interact with a coach and/or one another to more effectively follow a health regimen. A coach leading the matched group and/or the participants in the matched group may provide feedback and support tailored to the matched group overall and/or to individual participants in the matched group. In one preferred embodiment, the system guides participants diagnosed with prediabetes to lose weight to reduce their risk of developing diabetes. In particular, the system may be used to guide participants through the steps outlined in the Diabetes Prevention Program (a research study funded by the National Institute of Diabetes and Digestive and Kidney Diseases). The National Diabetes Prevention Program core educational course, core session handouts, post-core educational course, post-core session handouts, and additional materials (National Center for Chronic Disease Prevention and Health Promotion, Diabetes Training and Technical Assistance Center at the Rollins School of Public Health, Emory University) are incorporated herein by reference. In another embodiment, the system can help guide participants diagnosed with obesity to lose weight through an exercise and/or diet regimen. Furthermore, in alternative embodiments the system can collect other body metrics, such as BMI, body fat percentage, blood pressure, cholesterol, or other suitable measurements. In variations of the embodiments, the system can monitor weight loss or gain in other applications, such as to monitor rapid weight gain indicative of swelling after a diagnosis of congestive heart failure, to monitor unintended weight loss suggestive of paraneoplastic syndrome after a diagnosis of cancer (e.g., prostate or lung cancer), to monitor weight fluctuations after diagnosis of hyper- or hypothyroidism or hyper- or hypoadrenalism (which may indicate, for example, medication dosing errors or changes in the endocrine defect), or to monitor weight trends after diagnosis of eating disorders such as anorexia. In some alternative variations of the embodiments, the system 200 and/or method 100 may omit grouping the participants into at least one matched group, such that trends and feedback are determined on an individual basis only.

As part of the coaching with the social network, the system provides a rendering of the progress of the user. User progress in the form of visuals and/or analyzed metrics is shown as a source of motivation for the user following a health regimen. The progress feedback can display details and analyses of progress achieved by a given user in the health regimen such as a trend in a body metric measurement of the user, a trend in a body metric measurement of a user relative to that of a matched group, and/or a target goal in the health regimen for the user. The progress feedback may be further configured to display overall progress achieved by a user relative to certain earlier points and/or a starting point, a rate of progress (e.g. body metric change versus time), overall progress achieved by a user relative to a goal, and/or other personalized biometric data (e.g. current weight, height, age, body mass index). Preferably, the progress feedback is distinct from a profile page for a user; however, alternatively, the progress feedback and profile page for a user are non-distinct pages. In an example, using metrics determined from an exercise tracking biometric device, such as a watch that records run time and distance, the user interface can present progress (e.g., physical activity metrics) indicating that one user is underperforming relative to the established goal and/or relative to other users in the user subgroup. In a variation, the user interface can display progress in relation to sub-programs of a group program. Sub-programs can include one or more of: tasks (e.g., associated with diet, physical exercises, physical activity features, etc.), games, goals, and/or other suitable user actions. For example, a sub-program may include a task of "running for one hour for each day in the week", "practice yoga twice a week to reduce blood pressure", and/or "sleep eight hours per night during the week". In an example of displaying progress in relation to sub-programs, the system can be operable to determine a personal completion percentage for each human of the human subgroup based on a set of physical activity metrics (e.g., whether the physical activity metrics meet the weight loss goals and/or motion dataset-related goals associated with the sub-programs), where the personal completion percentage is associated with the set of sub-programs; and determine an aggregate completion percentage for the human subgroup based on the set of physical activity metrics (e.g., whether the aggregate weight loss of the user subgroup meets the aggregate weight loss goals, etc.); and where the user interface and/or other suitable component can be operable to present the personal completion percentage and the aggregate completion percentage. Additionally or alternatively, determining and/or presenting progress in relation to sub-programs.

In one embodiment, the Diabetes Prevention Program (a research study funded by the National Institute of Diabetes and Digestive and Kidney Diseases) can be used as educational training, but in alternative embodiments, the educational course page outlines steps or teaches lessons from other alternative health regimens. The training can display health regimen tips in the form of a lesson plan, including modules, milestones, and/or assignments. Preferably, the educational course page is configured to display the same educational course for all participants in a group participating in a health regimen; however, alternatively, the educational course page may be configured to display a educational course that is customized to a given user (e.g. based on user performance).

The social network enables a first user to connect with a second user and set up a meeting to perform a task associated with a health regimen training together. A coach may provide advice and motivational support to a user through the social network messaging software. In variations, the coach or third party may utilize the system to provide a modification to a sub-program (and/or associated aspects, such as user goals, therapeutic interventions, etc.) when a user is underachieving in the sub-program or a task associated with the sub-program.

In one aspect, a method for grouping a plurality of participants into a matched group; determining activities of the matched group members; and/or providing feedback to the user based on the activity metric of the user relative to the physical activity metric of the portion of the matched group. The matching of users into groups functions to establish a community among users that preferably share at least one common goal related to a body metric measurement, such as losing weight, maintaining weight, gaining weight, or reducing body fat percentage, and/or a common goal related to a health condition, such as preventing development of prediabetes to diabetes. Alternatively, the participants within a matched group are grouped based on another characteristic. In a preferred embodiment, a matched group includes approximately 8-16 participants, although the matched group may include any suitable number. Grouping a plurality of users may include one or more variations that cluster participants in similar or the same groups based on various shared characteristics.

One grouping can be based on a characteristic of a common goal. In a first example of the first variation, the participants within a matched group may share the goal of losing or gaining a certain percentage (e.g. 5%) of an individual respective starting weight or a certain number of pounds. In a second example of the first variation, the participants within a matched group may share the goal of maintaining current starting weight or to attain a particular goal weight. In other examples of the first variation, the participants within a matched group may share the goal of losing, gaining, maintaining, or attaining a particular level or amount of BMI, body fat percentage, or other body metric measurement.

In a second variation, the grouping can be based on medical history. In a first example of the second variation, participants within a matched group may be diagnosed with a particular condition at approximately the same time (e.g. diagnosed with pre-diabetes within two months of one another, or another suitable threshold). In a second example of the second variation, participants within a matched group may have similar initial body weights, similar initial degree (class or stage) of congestive heart failure or other diagnosis of a cardiovascular disease. In a third example of the second variation, participants within a matched group may be diagnosed with a similar degree of obesity, and in a fourth example of the second variation, participants within a matched group may be diagnosed with a similar stage of osteoarthritis or other joint disease that affects mobility. Other aspects of medical history may be considered in matching participants, such as diagnosis of depression or obsessive-compulsive disorder.

In a third variation the grouping can be based on shared personality traits, or similar positions within a personality spectrum. In an example of the third variation, participants within a matched group may have received similar results of a personality test or other assessment. Shared personality traits may include, for instance, optimism, extroversion, openness, agreeableness, or neuroticism. Grouping participants into a matched group may include administering to the participants a standard personality test (e.g. Myers-Brigg personality test, Big Five personality test) or a customized personality test, and clustering participants into matched groups based on the results of the standard or customized personality test.

In a fourth variation the grouping can be based on a shared lifestyle characteristic or common interests. In an example of the fourth variation, participants within a matched group may have similar dietary restrictions or preferences (e.g., vegetarianism, veganism, nut-free, gluten-free), marriage status (e.g., married, divorced, widowed, single), children status (e.g. existence, age, gender, number of children), pet status (e.g. existence, age, species, number of pets), religious identification, or other suitable lifestyle characteristic. In another example of the fourth variation, the participants within a matched group may have similar hobbies or other interests (e.g. sports, television shows, cooking).

In a fifth variation the grouping can be based on gender, ethnicity or nationality, age, current geographical area, other location characteristics, or occupational field. As another example of the fifth variation, personal information may include hometowns, schools attended, employers, or any suitable personal information.

In additional variations the grouping participants may incorporate any suitable combination of these variations and/or any suitable aspect of the participants. In some embodiments of the method, the participants may additionally and/or alternatively be grouped based on contrasting or complementary aspects, rather than all common traits. For example, participants within a matched group may include both optimists and pessimists, or extroverts and introverts. Furthermore, the step of grouping participants may include weighting one or more of the various characteristics more heavily than others in their importance in the grouping process. For example, grouping participants based on a characteristic of a common goal is preferably weighted more heavily than grouping participants based on personal information.

Grouping may further include sorting the participants using a "tiered" or "staged" process that effectively places the various characteristics in a hierarchy of importance. For instance, in a first stage an initial group of participants may filtered into a second group of participants that exclusively share the goal of losing a particular percentage of their initial respective weights. In a second stage, the second group of participants may be further filtered into a third group of participants that are within a particular age range. In a third stage, the third group of participants may be further filtered into a fourth group of participants that are of the same gender. In this manner, the grouping process may include any suitable number of stages that successively reduce or sort a larger group of participants into smaller matched groups until one or more suitable matched groups are created. In another embodiment, grouping may additionally and/or alternatively include assigning each of the participants a classification or number based on the sorting characteristics and grouping the participants based on their respective classification or number. However, the sorting characteristics may be used to group participants into appropriate matched groups in any suitable manner.

The system receives and stores a set of body metric measurement data over the network from the user and a portion of the participants of the matched group functions to gather data from which to generate feedback in support of the health regimen. This step is preferably repeated over time such that a time series of body metric measurement data may be received in regular intervals (e.g., hourly, daily, weekly, biweekly) or irregular intervals from the user and at least one other user of the matched group. The set of body metric measurement data may further include multiple time series of body metric measurement data, the multiple time series of body metric measurement data including a time series from the user, and a time series from each user of the portion of the matched group. Measurements from the user and from each user of the portion of the matched group may be received at the same time or at different times; preferably, measurements from the user and from each user in the portion of the matched group are received at the same frequency and/or simultaneously. Alternatively, measurements from the user and from each user in the portion of the matched group are received at different frequencies and/or different instances. As described above, the multiple time series are preferably received over a network such as a Global System for Mobile Communication or Wi-Fi. Each body metric measurement in the set of body metric measurement data is preferably labeled with identifying information, such as date, time, and/or location of measurement, personal information identifying the user being measured, and/or a serial number or other identifier of the body metric measurement device. A time series of measurements is preferably received with push technology, such that the measurement device of a user initiates transmission of body metric measurement data. However, the time series of measurements may additionally and/or alternatively be received with pull technology, such that the receiver initiates transmission of the body metric measurement (e.g. through polling or manual initiation on the receiver side). A time series of body metric measurements may be received as individual measurements, or as packets or bundles of multiple measurements.

In storing the set of body metric measurement data, the system can filter the received set of body metric measurement data, which functions to remove any suspicious measurements from the received measurement data. In particular, filtering preferably includes identifying erroneous measurements. Example erroneous measurements include measurements that are unlikely to come from a user (e.g. measurements resulting from outsider interference), erroneous measurements due to device malfunction, erroneous measurements due to user error, and other non-representative measurements. In one embodiment, the method may further include detecting if an outsider has used the device (e.g. through identity verification), so as to produce an erroneous measurement.

Determining a physical activity metric of the user functions to determine one or more metrics indicative of the progress and/or status of the user in the health regimen (e.g., as a function of time), in relation to a user status of the user, and/or in relation to any suitable aspect associated with the user. Physical activity metrics can include one or more of: weight-related metrics (e.g., weight, average weight over time, percentage weight loss in relation to a weight loss goal, BMI, weight metrics in relation to a user subgroup, etc.), motion-related metrics (e.g., in forms analogous to weight-related metrics), body metric measurement trends (e.g., generated from a series of a body metric measurement data points collected over time; across a plurality of users in a user subgroup; etc.), other physical activity-related metrics derived from body metric measurement data, and/or any other suitable metrics.

Determining physical activity metrics is preferably based on one or more body metric measurement datasets (e.g., bioimpedance datasets, EKG datasets, weight datasets, motion datasets, etc.), but can additionally or alternatively be based on one or more of: user subgroups (e.g., body metric measurement datasets for other users in the user subgroups; aggregating total weight loss over a period of time across the users in a user subgroup; otherwise combining datasets across users in a user subgroup to indicate progress for an individual user or set of users associated with a user subgroup; etc.), biomarkers, therapeutic interventions (e.g., determining physical activity metrics indicating effectiveness of a promoted therapeutic intervention, etc.), user demographics, user responses to surveys, and/or any other suitable data. In a variation, determining a physical activity metric can include: obtaining, applying, and/or otherwise manipulating a computer-implemented rule operable to improve processing by the medical improvement system (e.g., of body metric measurement datasets). Computer-implemented rules can include feature engineering rules, user preference rules (e.g., privacy rules associated with the types of body metric measurement datasets can be used, shared, and/or otherwise processed, etc.), user subgroup determination rules (e.g., parameters for matching users to user subgroups), coach matching rules (e.g., for assigning a coach to a user subgroup), therapeutic intervention rules (e.g., for promoting therapeutic interventions), and/or any other suitable computer-implemented rules enabling performance of the method 100. In a specific example, the method 100 can include generating a physical activity feature (e.g., an amount of weight loss and degree of physical activity over the past week) from evaluating the first weight dataset and the motion dataset against the feature engineering rule; and generating the physical activity metric (e.g., a cardiovascular health metric, etc.) based on the physical activity feature. However, computer-implemented rules can be used in facilitating any suitable portion of the method 100 (e.g., extracting features for determining therapeutic interventions, etc.), and can be configured in any suitable manner.

The system can assess the progress or status of the matched group in the health regimen. Determining a physical activity metric of a portion of the matched group preferably includes determining a physical activity metric based on a set of body metric measurement data representing all participants in the matched group or alternatively, less than all participants in the matched group. The physical activity metric for the portion of the matched group may be calculated in a manner similar to calculating the physical activity metric of a single user using any suitable variation as described above, except that each measurement/data point for the portion of the matched group may be an averaged (e.g., mean or median) measurement value of all of the participants within the matched group. In a first example using averaged measurement values, a time series of body metric measurement data may be collected from each user of the portion of the matched group, and measurements taken at similar time points (e.g. within a 24-hour period of time in a 16 week time period) may be averaged across all participants of the portion of the matched group for use in determining the physical activity metric of the matched group. In a second example using averaged measurement values, the physical activity metric of the matched group may include a different number of measurements than the number of measurements used to determine a physical activity metric in a body metric measurement of the user S150, as measurements from the participants in the portion of the matched group may not be available for identical periods of time (e.g. measurements are received once per day from one user and once every two days from another user). In the second example, the physical activity metric of the matched group may include a set of measurements, each representing an average group value over a two-week period, while the physical activity metric of the user may include a set of measurements, each measurement representing a daily value. However, both the physical activity metric of the user and the physical activity metric of a portion of the matched group may have any suitable resolution of measurement data points. In a third example averaged measurement values, each corresponding to different time points for the portion of the matched group, may be fitted to a line, such that a rate of progress of the portion of the matched group (e.g. weight loss per unit time) may be used to represent the physical activity metric of the portion of the matched group. Preferably, the user is a part of the portion of the matched group, such that the body metric measurement data of the user is factored into determining the physical activity metric in the body metric measurement data of the portion of the matched group; however, alternatively, the physical activity metric in the body metric measurement of the portion of the matched group may be determined from a subset of the set of body metric measurement data, where the subset excludes the body metric measurement data of the user. In variations, portions of the method can be performed based on, in relation to, and/or in any suitable relationship to physical activity metrics satisfying threshold conditions (e.g., a weight loss rate falling below a threshold condition).

Providing feedback to the user based on the physical activity metric functions to use the physical activity metric to support and motivate a user during his or her health regimen. Preferably, the user is a part of the matched group, such that the user is motivated by fellow "team members" in the matched group to adhere to the health regimen. In a variation, the user, as part of the matched group, "competes" against other matched groups as a source of support and motivation during his or her health regimen. Alternatively, the user is not a part of the matched group, such that the user "competes" against the matched group as a source of motivation during his or her health regimen. Preferably, feedback is provided through a user interface (described further below in more detail) communicatively coupled to at least one server that stores body metric measurements of the participants. The user interface is preferably an application accessed through a computing device, or alternatively, a website presented as a separate online social network site or online community. The user interface may alternatively be hosted by a third-party social network site. Providing feedback may include one or more of several steps as described below; however, the feedback may be provided in any suitable manner.

The providing feedback to the user can include displaying the physical activity metric in the body metric measurements of the user and/or displaying the physical activity metric in the body metric measurements of the matched group. One or both of these physical activity metrics may be displayed on a profile page of the user in a user interface. The physical activity metrics are preferably displayed on charts as a function of time, with any suitable time divisions (e.g., daily, biweekly, weekly, monthly). The physical activity metrics may additionally and/or alternatively be displayed as tables, bar graphs, or in any other format. In an embodiment, the method 100 follows a designated health regimen program such as the Diabetes Prevention Program, and providing feedback to the user S160 further includes displaying individual and/or group progress in the health regimen program and metrics of any activities associated with the health regimen, such as walking (e.g. determined using a connected pedometer). Simultaneously displaying physical activity metrics of a user and of the matched group enables the user to directly compare his or her progress and success in the health regimen with that of other participants, at least relative to the overall progress of the matched group. The overall progress of the matched group and individual progress of other participants in the matched group may be motivational to a particular user, and are preferably relevant to a particular user because of the nature in which the participants were sorted and grouped.

The feedback to the user can include enabling a coach associated with the matched group to access the physical activity metric of the user and/or the physical activity metric of the portion of the matched group. Similarly, providing feedback to the user preferably further includes enabling one or more of the participants in the matched group to view a displayed physical activity metric of another user and/or the physical activity metric of a portion of the matched group. However, providing feedback to the user may further include allowing the user to designate privacy settings that limit the details available to other participants and/or the coach. For example, the user may select settings such as to enable the coach and/or other participants to view a physical activity metric of his weight measurements represented in percentage of change, but to restrict the coach and/or other participants from viewing a physical activity metric of his/her weight measurements represented in absolute numbers.

The feedback can include promoting one or more therapeutic interventions, which functions to determine, provide, and/or otherwise facilitate therapeutic intervention provision to one or more users for improving user status. Promoting therapeutic interventions can include one or more of: generating control instructions (e.g., for operating one or more treatment systems, weight sensor subsystems, motion sensor subsystems, etc.); communicating with devices (e.g., transmitting control instructions, user interface components; receiving sensor data from treatment systems; etc.); controlling and/or operating system components; retrieving data (e.g., body metric measurement datasets for users of a user subgroup based on a user subgroup identifier, in order to generate an aggregate physical activity metric; etc.); and/or any other suitable operation. Types of therapeutic interventions can include any one or more of: physical activity-related notifications (e.g., including educational course components, physical activity metrics, etc.); physical exercises, mental exercises; interactions with facilitators; medication interventions; mobile device and/or treatment system-related interventions (e.g., modifying device operation parameters; etc.); ambient environment interventions (e.g., modification of light parameters, air quality and/or composition parameters, temperature parameters, humidity parameters; etc.) and/or any other suitable types of interventions. In an example, promoting a therapeutic intervention can include activating an application executable on a mobile device associated with the user; and providing the therapeutic intervention through the application (e.g., in association with presenting the visual representation of the physical activity metric at the application, such as in parallel, in serial, etc.).

The therapeutic interventions is preferably based on one or more physical activity metrics (e.g., recommending an increased frequency of outdoor walks based on a physical activity metric indicating a lower than average number of footsteps relative the user subgroup, etc.), but can additionally or alternatively be based one or more of: user demographic (e.g., therapeutic interventions correlated with positive outcomes for particular demographics, etc.), user subgroup (e.g., tailored to the shared physical activity characteristics of the user subgroup, tailored to involve communications and/or other suitable interactions, such as group exercise classes, between users of the user subgroup and/or facilitators for the user subgroup, etc.), therapeutic intervention effectiveness (e.g., adjusting therapeutic interventions, such as medication regimen aspects based on user response to administered medication), and/or any other suitable criteria (e.g., data used in determining physical activity metrics, etc.). In examples, the therapeutic intervention can include a personalized therapeutic intervention for the user (e.g., determined based on the physical activity metrics generated specifically for the user based on collected body metric measurement datasets for the user, etc.).

The coach associated with the matched group can communicate with one or more of the users in the matched group. For example, promoting a therapeutic intervention can include: enabling a wireless communication link between a coach device and a user device, where the coach device is associated with a coach for the user subgroup, and where the user device is associated with the first user; and facilitating a video communication between the coach and the first user over the wireless communication link. As shown in FIG. 6, in another example, the coach may address general comments to the matched group on a group page of a user interface. The coach may additionally and/or alternatively provide targeted comments to a particular individual user, such as by posting comments on the profile page of the user, and/or by sending a personalized message accessible only by the individual user and the coach. Similarly, providing feedback may further include enabling a user in the matched group to provide comments to one or more of the other participants in the matched group, including general comments on the group page, targeted comments on the profile page of a particular targeted user, and/or personalized messages accessible only by the user and the targeted user. Comments from the coach and fellow participants in the matched group serve to provide motivation and support throughout the health regimen. Such comments may include, for example, congratulatory remarks on a completed milestone, suggestions for modifications in activities (diet, exercise plan, etc.), general motivational remarks, sharing of personal stories to enhance personal connections within the matched group and/or coach, questions to generate discussions, invitations to perform a health regimen educational course task socially, or any suitable comments. In some embodiments, providing feedback further includes enabling a coach and/or users in the matched group to share photos or other media with another user or the matched group in general. However, communications between users and/or facilitators can be in any suitable form (e.g., visual, audio, haptic, textual, virtual reality, etc.). Further, facilitating communications can be performed in any suitable manner.

In a variation, promoting a therapeutic intervention can include providing a health regimen training (e.g., to each user of the matched group, etc.), which functions to change a participant's eating and activity in order to achieve a goal. In a first example, the health regimen educational course includes steps outlined in the Diabetes Prevention Program (a research study funded by the National Institute of Diabetes and Digestive and Kidney Diseases), and providing a health regimen educational course includes presenting steps based on the Diabetes Prevention Program as lessons through a user interface. The lessons may be organized into four phases, including: a first phase involving changing food habits, a second phase involving increasing activity levels, a third phase involving preparing for challenges, and a fourth phase involving sustaining healthy choices; furthermore, the user may be encouraged to set goals and meet milestones, as well as complete assignments (e.g. journal entries, meal experiments) as part of the health regimen educational course in the first example. The first example providing each of the four phases of lessons may be accompanied by providing a kit corresponding to each phase, where the first phase kit includes a body metric measurement device such as the vital sign sensors, the second phase kit includes a second measurement device and tool (e.g. a pedometer and a food tracking tool), the third phase kit includes motivational prizes (i.e. upon graduating from the educational course), and the fourth phase kit includes materials to support the user in sustaining healthy choices (i.e. post-graduation).

In another example, providing a health regimen training/educational course may include providing a diet modification and exercise routine regimen including daily meal plans and exercise tasks geared to treat a diagnosed condition, such as cardiovascular disease or diabetes. In a third example, providing a health regimen educational course may include providing a physical therapy regimen educational course. In other examples, providing a health regimen educational course may include providing any appropriate health regimen educational course for a given condition, that is preferably fixed, or alternatively, customizable by a user, coach, or automatically to meet the participant's specific needs. The health regimen may be customizable by a coach or automatically, such that if the user is not making progress at a rate comparable to that of a matched group, the health regimen may give the user additional feedback and advice so that the user is given an advantage or "handicap" relative to the matched group. The customized health regimen may be provided based on a performance metric of the user, such as absolute change in body weight relative to an initial baseline measurement (after a period of time has elapsed from initiation of the regimen) or an unmet goal set by the user and/or a coach.

In another variation, promoting a therapeutic intervention can include providing a physical motivational incentive to the user, which functions to promote adherence to the health regimen educational course. Providing a physical motivational incentive to the user S180 may include providing health-related physical awards, such as coupons, nutritional supplements, and/or exercise equipment. In an example, providing a physical motivational incentive to the user S180 may be performed after the user has reached a health regimen goal/milestone, or if the user experiences a quantifiable level of progress above a specified threshold. In an alternative example, providing a physical motivational incentive to the user may be performed if the user is not making progress at a rate comparable to that of a matched group, such that the user is given an advantage or "handicap" relative to the matched group to equalize chances of success relative to the matched group. The physical motivational incentive may be provided based on a performance metric of the user, such as absolute change in body weight relative to an initial baseline measurement (after a period of time has elapsed from initiation of the regimen) or an unmet goal set by the user and/or a coach.

In some alternative embodiments, the method may omit matched groups. For example, displaying feedback may include displaying the physical activity metric of a body metric measurement of a user on the profile page of that user, but not displaying a physical activity metric of the body metric measurement of any other user or group of participants.

Exercise Coaching

In addition to coaching the user to maintain a condition such as glucose within a predetermined range, the system can also coach the user to strengthen and improve the muscles. In one example, user wears one or more sensor device(s) during exercise (e.g., on the ankle while running, on arms and legs while swimming, etc.) to capture motion data and convert that exercise into calorie consumption and glucose level. For example, for those with high blood pressure and diabetic condition, walking can help people with type 2 diabetes lower their blood sugar levels and lose weight. Diabetic neuropathy, a condition that occurs when the nerves become damaged, can also cause joint pain in people with type 2 diabetes. A low-impact exercise such as cycling can be done to meet fitness goals while minimizing strain on joints. Swimming, water aerobics, aqua jogging, and other aquatic activities can give heart, lungs, and muscles a workout, while putting little stress on your joints and can help lower blood sugar levels, much like land-based exercise does. Yoga can help people with type 2 diabetes manage their blood sugar, cholesterol levels, and weight. It might also help lower blood pressure, improve the quality of sleep, and boost mood.

The system can determine the impact of a particular set of exercise on a health condition and guide the user to perform an exercise, including counting a number of repetitions, a duration of a static movement, and providing feedback regarding the exercise. The exercise can be guided by an application installed on a mobile device such as a phone. The user wears one or more sensor devices on his wrist, ankle, arm, or any other appropriate part of the body or equipment. As further described herein, in some embodiments, the sensor is worn in a body region that is expected to be in motion during the exercise. In other embodiments, the sensor is worn in a body region that is expected to be substantially static during the exercise. The user's motion is processed to identify and analyze stages of an exercise, including: a preparation stage, back and forth motion of each repetition ("rep" for simplicity), staying in static motion, fatigue, and/or a termination stage. For example, a user may terminate the exercise due to giving up, running out of time to complete the exercise, and the like. With this information, the management device can give context-aware coaching feedback to the users, for example, to count, to motivate and to give instructions on the exercise. The exercise is typically structured as a circuit training program but can be used in any workout structure.

As will be described in greater detail below, a sensor device includes one or more accelerometers and one or more gyroscopes, and, optionally, one or more magnetometers. The sensor device is configured to take measurement data samples of acceleration, angular velocity, and, optionally magnetic field in connection with the user motions. In some embodiments, the accelerometer(s), the gyroscope(s), and the magnetometer(s) are implemented using one or more integrated circuits (ICs). The device 102 can provide feedback such as information about the user's form, the difference between the user's form and the target, what the user can do to improve his form, etc.

In one embodiment, the CPU/GPU determines, based at least in part on the motion data samples, velocity and orientation associated with a subset of the user's motions. The motion data samples include a set of acceleration data samples taken by the accelerometer, a set of angular velocity data samples taken by the gyroscope, and, optionally, a set of magnetic field data samples taken by the magnetometer. The samples are taken while a user wearing one or more sensor devices is performing a set of exercise motions. For example, while running, the user wears a sensor device on his leg to capture motion data of the leg's movements; while swimming, the user wears a sensor on his arm to capture motion data of the strokes made by the arm, and a sensor on his leg to capture motion data of the kicks made by the leg. Additional sensor devices can be worn so that motion data of both sides of the body is captured. The samples are taken while a user wearing one or more sensor devices is performing a set of exercise motions. For example, while running, the user wears a sensor device on his leg to capture motion data of the leg's movements; while swimming, the user wears a sensor on his arm to capture motion data of the strokes made by the arm, and a sensor on his leg to capture motion data of the kicks made by the leg. Additional sensor devices can be worn so that motion data of both sides of the body is captured.

In one embodiment, a neural network can be used to detect motion and determine the kinematics. Based on kinematic analysis, the sequence of motion can be determined and a repetition count can be made. For example, one or more sequence of motion data samples can be analyzed to determine movement points corresponding to a particular motion to determine a rep. The sensor sends the user's arm or foot motion to the CPU/GPU or to the local computing device 104. By comparing the motion path to a target motion path, the CPU determines whether to increase the repetition count. Verbal feedback can be provided to a user and may include information about the user's progress such as the current rep count, the total reps completed so far, the number of reps remaining to meet a goal, a number of calories burned so far, and the like. For example, the user may be told and/or shown how much he is off target, and be given tips on how to adjust the movements to achieve target. In some embodiments, a trained feedback model is used to intelligently provide feedback based on the evaluation result. The feedback can be based at least in part on a comparison between a form measurement and a target.

To start an exercise, a baseline pose of the user is determined. In some embodiments, the baseline pose is used to count the number of reps. The baseline pose may take into account the attributes of a user such as flexibility, strength, and endurance. For example, when the exercise is jumping jacks, a baseline pose is standing with feet together and hands at the side. Reps can be counted based on subsequent returns to this baseline position. The user is asked begin the exercise through a visual signal, an audio signal, a haptic signal, or the like. The user is instructed to begin the exercise, e.g., start the workout. In an embodiment, the workout is a dynamic motion, where the user moves between a plurality of states. For example, for a jumping jack, the user moves back and forth between two states: first standing with feet together and hands by the side, then standing with feet apart and hands over the head. A user typically transitions between the two states by jumping from one to the other in a continuous motion. One cycle through the two states is counted as one rep. When performing different exercises (e.g., sit-ups, push-ups, etc.), the user may transition between different states. In another embodiment, the workout is a static motion such as a plank.

Because the reps involve repetitive activity, a neural network can learn the data associated with a particular motion based on a particular user pattern for removing or reducing any inaccuracies in the data samples received from the sensors. Since exercise motions are often repetitive, in some cases, each core measurement measures the body positions of the user during a single repetition of the exercise motions (e.g., a single step during running, a single stroke during swimming, a single punch during boxing, etc.). Examples of form measurements include cadence, stride, range of motion, efficiency, speed, landing impact, pronation, etc. The form measurements can be instantaneous measurements of a single motion rather than averages of a series of motions. For example, the user's instantaneous stride is determined by measuring how much time it takes for him to run a single step, and the cadence is the reciprocal of the stride; the user's instantaneous range of motion is determined by measuring the maximum angular motion of his leg between the most forward and most backward positions; the user's instantaneous efficiency is determined based on the energy concentration of the angular velocity; the user's instantaneous speed is determined based on velocity; the user's landing impact is determined based on acceleration; the user's pronation is determined based on the orientation, and so on. As discussed above, the evaluation can be performed by the sensor device or by the management device. In some embodiments, multiple form measurements are used to further derive other form information, such as the average, mean, maximum, minimum, standard deviation, etc. In some embodiments, the core measurements are used directly as form measurements. For example, during a boxing exercise, the velocity and orientation measurements are used to measure the user's form in delivering a punch.

One embodiment uses machine learning to analyze user activity stats—calories and heart rate, among other metrics—and offer tailored advice. Personalized coaching can be done for running, swimming, cycling, boxing, and interval training. An artificially intelligent assistant audibly guides the user through the selection of variations of workouts and, during the workout, lets you know how well the user is doing—whether the user needs to jog faster or bike harder to meet the daily fitness goal, for instance. The user can ramp up the intensity of a workout in progress, or turn on a "reduced coaching" mode (that is, tell the thing to pipe down) if the user desperately needs a breather.

The coach can guide the user in heart-rate based HIT circuit workouts that rely on body weight exercises, and high intensity running workouts. The workouts also introduce a new program overview screen that lets users preview the exercises involved before they commence interval training. In addition, workout screens present a clearer picture of how users are performing during their workout, with more targeted advice on what they need to do to get the most benefit from the exercises. The system generates post-workout report cards also feature in the update, with greater granular data, clearer performance measures, and improved highlights. The coaching features, guides wearers through their workouts move by move to keep them in their optimal heart rate zone/magnetometer/gyroscope/accelerometer/BP/glucose data in one embodiment.

One embodiment determines a heart rate intensity (HR intensity) and to determine a real-time workload status: a sprint or compensating state if the HR reading or HR intensity significantly increases; an aerobic endurance state if the increased HR intensity is fixed within a zone wherein a HR intensity fluctuates between a range; and a dynamic recovery state if the HR intensity decreases about 1% to about 20% than the average HR intensity of the aerobic endurance state for a time period that is longer than that of the sprint or compensating state. The coaching can optimize HR intensity (also known as percent heart rate reserve, heart rate capacity, target heart rate, or % HRR). For example, the maximum heart rate (HRmax) is the highest heart rate an individual can safely achieve through exercise stress, and depends on age. The resting heart rate (HRrest) of an individual may be obtained by any suitable method including, for example, a heart rate measurement taken when the activity level of the individual is sufficiently low to be considered inactive. Alternatively, the HRrest is an individual's heart rate when he/she is at rest, that is lying down but awake, and not having recently exerted themselves. The age compensated maximum heart rate can be calculated by the formula: (220-age). Other calculations of age-predicted maximal heart rate are provided by Hirofumi Tanake et al (J of Am college of Cardiology 2001: 153-6). The heart rate variability (HRV) generally refers to the beat-to-beat fluctuations in heart rate (e.g., variation in R-R interval) that occurs as a normal physiological response (e.g., an internal response to neuronal or endocrine influence), or variations in heart rate that occur in response to external stimuli. In general, heart rate variability reflects the non-invasively autonomic nervous system activity (e.g., the sympathetic and parasympathetic influences upon the heart beat's rate and rhythm). Short-term (beat-to-beat) variability in heart rate represents fast, high-frequency (HF) changes in the heart rate. For example, changes in heart rate associated with breathing are characterized by a frequency of between about 0.15 and about 0.4 Hz (corresponding to a time constant between about 2.5 and 7 seconds). Low-frequency (LF) changes in heart rate (for example, blood pressure variations) are characterized by a frequency of between about 0.04 and about 0.15 Hz (corresponding to a time constant between about 7 and 25 seconds). Very-low-frequency (VLF) changes in heart rate are characterized by a frequency of between about 0.003 and about 0.04 Hz (0.5 to 5 minutes). Ultra-low-frequency (ULF) changes in heart rate are characterized by a frequency of between about 0.0001 and about 0.003 Hz (5 minutes to 2.75 hours). A commonly used indicator of heart rate variability is the ratio of HF power to LF power. The coach can talk to the user during the sprint, the aerobic endurance, the compensating and the dynamic recovery statuses to coach the user's exercise. In one embodiment, a visual display can be used for displaying suggestions. For example, the suggestions displayed include (a) a suggestion regarding recovery and sprint, and (b) a suggestion regarding increase and reduction of velocity. The suggestion (a) is provided for determining whether to take dynamic recovery (reduce exercise strength) or sprint (increase exercise strength or speeding). The suggestion (b) is provided for the determining whether to increase or decrease velocity so that the user can best approach the predetermined target but within the user's physiological tolerance based on a predetermined target time and physiological situation. For example, the coach can verbally give notifications such as "increase speed," "reduce speed," "increase number of breaths," "reduce number of breaths," "deep breath" or "drink water."

According to one embodiment of the invention, the workout intension is calculated based on a resting heart rate (RHR) and a maximal heart rate (MHR) for a concerned age. The RHR is variable depending on different health condition which can be automatically detected by one or more of the sensors of the invention. On the contrary, the MHR is a fixed value. Alternatively, the user can enter a value to be defined as the RHR. Since the RHR may vary according to the user's health condition on a given day, the absolute value for workout intension may also vary. The range between RHR and MHR is divided into 10 parts. The current heart rate, the RHR and the MHR are used as parameters to calculate the current workout intensity. The RHR will vary depending on the user's health state and the environmental factors (such as temperature, air pollution and altitude etc.), so the range of heart rate for each part will be adjusted based on the RHR.

A coaching engine can be used with a plurality of agents or coaches which can be executed in sequence in the order the coaches are listed in the user coach list. The coaches can be listed in the order they are added to the list, with the root coach at one end of the list and the most recently added coach at the other end of the list. Coaching engine can first execute a root coach for a user, followed by execution of additional coaches in the order the coaches were added to the user coach list. Each coach instance, or coach, can retrieve rules and actions. The rules can be retrieved by a coach instance from a rule library stored on application server. Retrieving rules may include retrieving an expression having one or more attributes. The attributes can be retrieved from an attribute library stored on application server and the retrieved rules are then executed by the coach instance.

A coach instance can evaluate one or more expressions having attributes and operations. The attributes can include simple and calculated attributes, such as height, weight, sex, BMI, LDL, blood pressure, and so forth. When a coach instance is created from a coach object, the coach instance retrieves the rule expression as well as user health data to provide values for expression attributes. The user health data values are used to carry out the coach instance expression as part of the protocol associated with the particular coach instance. The operation can indicate an expression to perform on the attribute, such as calculate a value for, determine if the attribute has a value of true or false, determine if the attribute value is greater than or less than some value or other attribute, or some other operator. Thus, an expression that includes an attribute and an operation performed on the attribute can be evaluated to determine if a particular condition regarding the attribute exists. A trend function is a type of expression that evaluates the trend of an attribute value over time. A trend function can determine if a particular attribute value has increased over time, has surpassed a particular value a certain number of times over a time period, whether the attribute value experienced a particular rate of increase decrease over time, or some other trend. For example, a rule may perform an action of enlisting a user in a diet program if a user's body mass index has increased greater than a threshold rate over a period of time. Trend calculations can be evaluated using health data in several ways. A coach instance can determine a trend by comparing selected indicia of a series of data points such as a first value and a last value, comparing data points selected by identifying data points by time and date, or comparing the trend between a past date or current date and a delta of time.

When no specific data points correspond to a desired date and time for which a data value is needed for trend evaluation, the data points may be calculated using a set of guidelines. When there is only one data point for a particular attribute, the single value can be used for the desired date and time. If the trend of user's weight is desired over the last three months but the only available weight data point is for a date three months ago, the previous value of the user's weight can be used for both a previous value and current value thus resulting in a trend of zero change. If the date and time for a desired attribute data point is after the most recent value for the attribute, then the most recent attribute value is used for the required attribute data and time. If the date and time for a desired attribute data point is before the first known value for the attribute, then the first known attribute value is used for the required attribute data and time. If the attribute date and time is between two existing attribute value dates, then the two attribute values that surround the desired attribute date and time can be linearly interpolated to determine the attribute value at the required date and time.

Once a coach instance is created and the coach rule is evaluated, a determination is made as to whether the expression is evaluated to be true. A coach expression can be constructed as a condition, such as whether a particular attribute value is within a particular range, whether a user has performed an action, or some other condition. The operators to form the condition may be retrieved by the coach instance from an operator library stored on application server. Evaluating the expression condition can result in a value of true if the condition is met or false if the condition is not met. If a rule expression for a coach is evaluated to be true, the coach instance containing the expression determines the last time the action corresponding to the expression was performed. For expressions evaluated to be true, the date the corresponding action was last performed is compared to a periodicity period for the expression by the coaching instance. The comparison is performed to determine if the action should be performed in response to the most recent expression evaluation. The periodicity period can indicate the maximum frequency at which the action can be performed. If the time period between the last performance of the action and the current time is less than the periodicity period, the action is not performed. If the time period since the last time the action was performed is greater than the periodicity period, the action corresponding to the evaluated expression can be performed by the coach instance.

Figure 4:
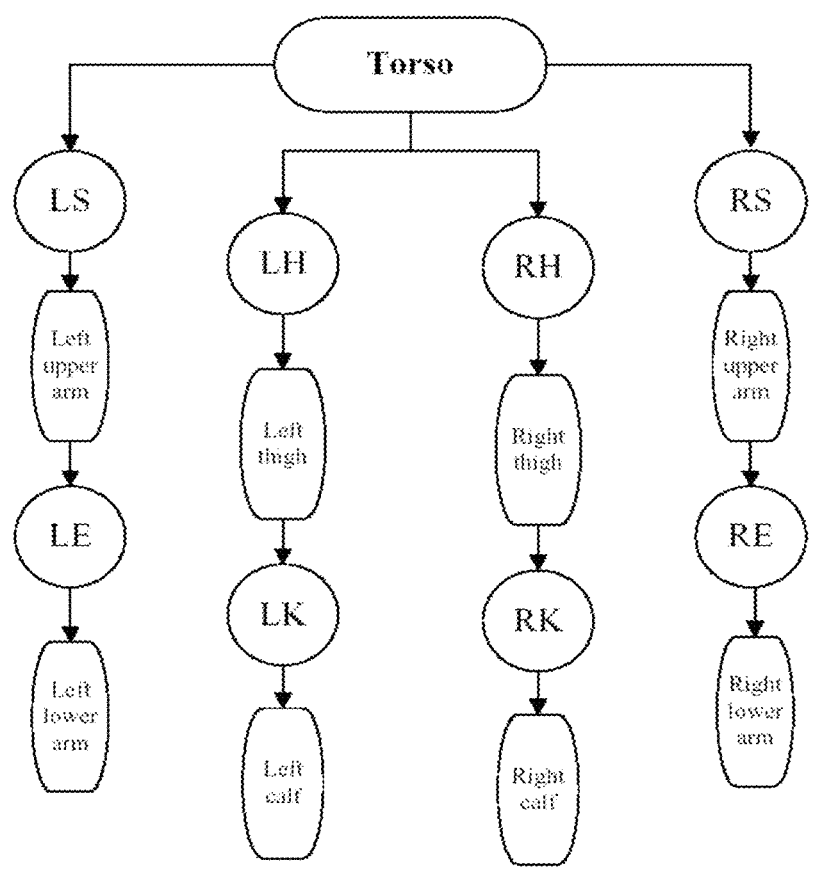
FIG. 4 shows an exemplary kinematics modeling system to model user exercise and resulting calories burned based on the kinematics model.

FIG. 4 shows exemplary kinematic modeling of user activity or lack thereof. With accelerometers and gyroscopes, the system can analyze user locomotion, which requires the measurement and analysis of the following: Temporal characteristics, Electromyographic signals, Kinematics of limb segments, and Kinetics of the foot-floor and joint resultants. Temporal analysis of gait in the person provides some norms for the average velocity of walking as well as time durations for the two phases of gait: the stance phase and the swing phase. The symmetry and asymmetry of gait can be captured by the accelerometer. The system can model the kinematics or relative motion that exists between rigid bodies, known as links between the body and the legs. Kinematic analysis of gait involves accelerometers positioned at different body parts to capture the displacement, velocity, and acceleration of various body segments. A model of the links and their movements can be created for diagnosis and also for real time assistance if needed. The model can also be used for energy consumption analysis, athletic training, and predictive health for particular tasks. In one embodiment, the gaits of the user are commonly used patterns of locomotion that can be divided into two main groups: symmetric and asymmetric. With symmetric gaits such as the walk, trot, and pace, the movement of the limbs on one side of the user body repeats the motion of the limbs on the opposite side with the intervals between foot falls being nearly evenly spaced. With asymmetric gaits such as the competitive running for person or gallop for a horse, the limb movements of one side do not repeat those of the other and the intervals between foot falls are unevenly spaced. When considering gaits, one full cycle is referred to as a stride. The motions as captured by the sensors of FIG. 1 can be used to determine user activity, which translates to accurate calorie burning.

In addition to providing beat-to-beat timing information for other sensors to use, the patterns of the constituent waveform features determined by the HMM or neural networks, among other classifiers, can be used for detecting heart attacks or stroke attack or out of control glucose level, among others. For example, the detection and classification of ventricular complexes from the ECG data is can be used for rhythm and various types of arrhythmia to be recognized. The system analyzes pattern recognition parameters for classification of normal QRS complexes and premature ventricular contractions (PVC). Exemplary parameters include the width of the QRS complex, vectorcardiogram parameters, amplitudes of positive and negative peaks, area of positive and negative waves, various time-interval durations, amplitude and angle of the QRS vector, among others. The EKG analyzer can analyze EKG/ECG patterns for Hypertrophy, Enlargement of the Heart, Atrial Enlargement, Ventricular Hypertrophy, Arrhythmias, Ectopic Supraventricular Arrhythmias, Ventricular Tachycardia (VT), Paroxysmal Supraventricular Tachycardia (PSVT), Conduction Blocks, AV Block, Bundle Branch Block, Hemiblocks, Bifascicular Block, Preexcitation Syndromes, Wolff-Parkinson-White Syndrome, Lown-Ganong-Levine Syndrome, Myocardial Ischemia, Infarction, Non-Q Wave Myocardial Infarction, Angina, Electrolyte Disturbances, Heart Attack, Stroke Attack, Hypothermia, Pulmonary Disorder, Central Nervous System Disease, or Athlete's Heart, for example.

In one embodiment to detect stroke, 3D accelerometer sensing is used. First, the process looks for weakness (hemiparesis) in either the left half or the right half of the body, for example the left/right arms, legs, or face (3000). Next, the system analyzes walking pattern to see if the patient has a loss of balance or coordination (3002). The system then asks the user to move hands/feet in a predetermined pattern (3004) and reads accelerometer output in accordance with predetermined pattern movement (3006). For example, the system can ask the user to point his/her right or left hand to the nose. The accelerometer outputs are tested to check if the correct hand did reach the nose. In another example, the user can be prompted to extend his or her hands on both side and wiggle the hands or to kick the legs. Again, the outputs of the accelerometers are used to confirm that the user is able to follow direction. The accelerometer, ECG, and glucose sensor outputs are provided to a pattern classifier, which can be an HMM, a neural network, a Bayesian network, fuzzy logic, or any suitable classifiers (3008). The system also checks whether patient is experiencing dizziness or sudden, severe headache with no known cause (3010). Next, the system displays a text image and asks the patient to read back the text image, one eye at a time (3012). Using a speech recognizer module, the user speech is converted into text to compare against the text image. The speech recognizer also detects if the user exhibits signs of confusion, trouble speaking or understanding (3014). The system also asks the patient if they feel numbness in the body—arms, legs, face (3016). Next the system asks the patient to squeeze gauge/force sensor to determine force applied during squeeze (3018).

In one implementation, an HMM is used to track patient motor skills or patient movement patterns. The muscular groups attached at various locations along the skeletal structure often have multiple functions. The majority of energy expended during walking is for vertical motion of the body. Wireless sensors with tri-axial accelerometers are mounted to the patient on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others. The sequence of human motions can be classified into several groups of similar postures and represented by mathematical models called model-states. In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the patient through additional tests to confirm a stroke attack, and if a stroke attack is suspected, the system prompts the user to seek medical attention immediately and preferably within the 3 hour for receiving TPA.

In an exemplary process for determining weakness in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others. The system can ask the patient to squeeze a strength gauge, piezoelectric sensor, or force sensor to determine force applied during squeeze. The system can detect hemiparesis, a very common symptom of stroke, by detecting muscular weakness or partial paralysis to one side of the body. Additionally, the accelerometers can detect ataxia, which is an impaired ability to perform smooth coordinated voluntary movements. Additionally, the system can detect aphasia, including receptive aphasia and expressive aphasia. Aphasia is a cognitive disorder marked by an impaired ability to comprehend (receptive aphasia) or express (expressive aphasia) language. Exemplary embodiments are disclosed for detecting receptive aphasia by displaying text or playing verbal instructions to the user, followed by measuring the correctness and/or time delay of the response from the user.

Depending on the severity of the stroke attack or out of control glucose level, patients can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Patients with pure motor hemiparesis present with face, arm, and leg weakness. This condition usually affects the extremities equally, but in some cases, it affects one extremity more than the other. The most common stroke location in affected patients is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Patients with clumsy-hand dysarthria syndrome experience unilateral hand weakness and dysarthria. The dysarthria is often severe, whereas the hand involvement is more subtle, and patients may describe their hand movements as "awkward." This syndrome is usually caused by an infarct in the pons.

Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

The system can detect a pattern of motor weakness. Ischemia of the cortex supplied by the middle cerebral artery typically causes weakness that (1) is more prominent in the arm than in the leg and (2) involves the distal muscles more than the proximal muscles. Conversely, involvement of an area supplied by the superficial anterior cerebral artery results in weakness that (1) is more prominent in the leg than the arm and (2) involves proximal upper extremity (shoulder) muscles more than distal upper extremity muscles. Flaccid paralysis of both the arm and leg (unilateral) suggests ischemia of the descending motor tracts in the basal ganglia or brainstem. This is often caused by an occlusion of a penetrating artery as a result of small-vessel disease. Once the stroke is detected, intravenous (IV) tissue plasminogen activator (t-PA) needs to be given within 3 hours of symptom onset. An accurate assessment of the timing of the stroke is also crucial. The system keeps track of the timing off the onset of the stroke for this purpose.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer are used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the patient is at rest so that EMG data can be accurately captured or to compensate for motion artifacts in the EMG data in accordance with a linear or non-linear compensation table. In yet another embodiment, the EMG data is used to detect muscle fatigue and to generate a warning to the patient to get to a resting place or a notification to a nurse or caregiver to render timely assistance.

The amplitude of the EMG signal is stochastic (random) in nature and can be reasonably represented by a Gausian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In the above embodiments, the local computer 104 can perform the bioelectric signal processing to extract patient parameters from data captured by the contacts. In this case, the local computer may need a DSP or powerful CPU to perform the calculations. Alternatively, in an ASP model, the local computer 104 or sensor 102 can simply compress the data and upload the data to a central server or server farm for processing and the result of the signal processing are sent back to the base station for relay to the patient interface which can be a wrist-watch, a pad, or a band, among others, for notification of any warning signs.

Figure 5:
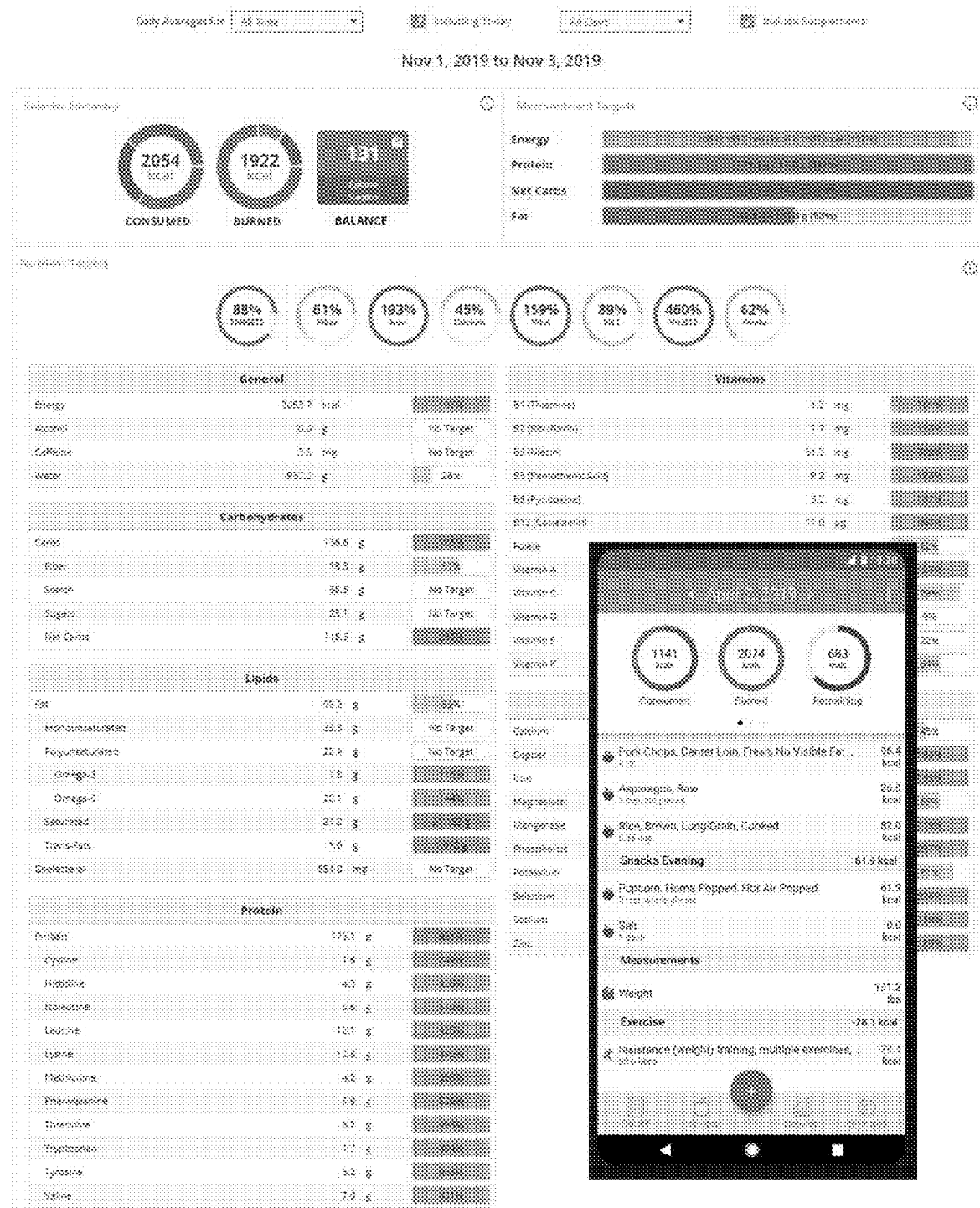
FIG. 5 shows an exemplary food data capture system.

FIG. 5 shows an exemplary food logging system that records in depth the amount of food and the macronutrients consumed. The food system monitors macro targets in an easy to read graphic format, the software also tracks micronutrients, including calcium (essential for bone health) to B vitamins (which are sometimes hard to get in a vegetarian or vegan diet), to folate (which is well-known for its importance during pregnancy for a baby's healthy brain development) and every other micronutrient. The software tracks a wide range of biometrics, from weight and waist size to cholesterol levels, triglycerides, ketones, ferritin, and 25-Hydroxy Vitamin D. It tracks blood pressure, pulse, body temperature, sleep and even mood. A Trends feature is for measuring how habits are evolving over time, and how their weight and other biometrics are affected. The food database is constantly updated by users who submit the nutrition information from foods they eat. Many packaged foods can be added by scanning their barcodes, and every day users are adding foods they incorporate in their diets. A team of experts reviews and corrects every entry before it is added to the public database. Each item also has its sources listed: from laboratory analysis, nutrition labels, or custom foods and recipes. The food data collected is then correlated with glucose level.

FIG. 6 shows learning system architectures for determining glucose, heart rate, blood pressure, among others. The same architecture can also recommend treatment based on sensor data captured over time and based on treatment data for a population of users. For example, during examination, a doctor uses a smartphone to review sensor data from a biologic such as a human or an animal. Feature extraction is done on the data as detailed herein. In parallel, clinical information such as sex, age, temperature, medical history, among others, are provided to feature extraction. As the data is text, the feature extraction can be done by extracting feature windows around a particular word of interest. The description can be vectorized into a sparse two-dimensional matrix suitable for feeding into a classifier. Feature hashing, where instead of building a hash table of the features encountered in training, as the vectorizers do, instances of FeatureHasher apply a hash function to the features to determine their column index in sample matrices directly. Since the hash function might cause collisions between (unrelated) features, a signed hash function is used and the sign of the hash value determines the sign of the value stored in the output matrix for a feature. This way, collisions are likely to cancel out rather than accumulate error, and the expected mean of any output feature's value is zero.

In addition, prior examination data can be featurized. At the time of a given exam, relevant information for predicting the diagnosis or prognosis may come not only from the current exam, but also from the results of past exams. The system combines information from the current and past exams when making a prediction of diagnosis or prognosis. If all users/patients received regular exams, for example, annually, it would be possible to simply generate one feature vector for the current exam, another for the exam from 1 year ago, another for the exam from 2 years ago, etc. Those feature vectors could then be combined via simple concatenation (possibly followed by dimensionality reduction) using the same procedure described herein to combine features within a single exam to form a combined feature vector. However, in general, patients may not be expected to all have had regular past exams on the same schedule. For example, patient A may have had annual exams, patient B may have had exams every other year, and patient C may have only had exams during periods of illness, which occurred at irregular intervals. Therefore, there is a need for a consistent method of converting information from past exams into a feature vector in a way that does not depend on the frequency or interval between past exams. One possible method for combining information from past exams is to combine features from past exams via a weighted average that takes into account the time from the current exam, with more recent exams weighted higher. For example, a linear weighting function could be used which linearly runs from 0 at birth to 1 at the present time. For an example patient of age 10 who had exams at ages 3 months, 9 months, and 6 years, each feature would be averaged together across exams (excluding the present exam), with weights of 0.025, 0.075 and 0.6. Weighting functions other than linear could be used (e.g., logarithmic, power law, etc.) and weights could also be normalized to add up to 1. Features from the current exam would also be included separately in the feature vector, concatenated together with the weighted features from past exams. Alternatively, one could include the current exam's features in the weighted feature vector from past exams, instead of including it separately. The generated feature vectors are then provided to a deep learning system.

One embodiment uses a conditional-GAN (cGAN) as a deep learning machine. The cGAN consists of two major parts: generator G and discriminator D. The task of generator is to produce an image indistinguishable from a real image and "fool" the discriminator. The task of the discriminator is to distinguish between real image and fake image from the generator, given the reference input image.

The objective of a conditional-GAN is composed of two parts: adversarial loss and LI loss. The adversarial loss can be: where LI distance is added to generated image. LI distance is preferred over L2 distance as it produces images with less blurring.

The ResNet-50 network by He et al. can be used as the generator, while the discriminator can be a convolutional "PatchGAN" classifier with architecture similar to the classifier in pix2pix as our discriminator.

In addition to cGAN, other neural networks can be used. Exemplary alternatives include 1. AlexNet—AlexNet is the first deep architecture which can be introduced by one of the pioneers in deep learning— Geoffrey Hinton and his colleagues. It is a simple yet powerful network architecture, which helped pave the way for groundbreaking research in Deep Learning as it is now.

2. VGG Net—The VGG Network can be introduced by the researchers at Visual Graphics Group at Oxford (hence the name VGG). This network is specially characterized by its pyramidal shape, where the bottom layers which are closer to the image are wide, whereas the top layers are deep.

VGG contains subsequent convolutional layers followed by pooling layers. The pooling layers are responsible for making the layers narrower. In their paper, they proposed multiple such types of networks, with change in deepness of the architecture.

3. GoogleNet—In this architecture, along with going deeper (it contains 22 layers in comparison to VGG which had 19 layers), the Inception module is used. In a single layer, multiple types of "feature extractors" are present. This indirectly helps the network perform better, as the network at training itself has many options to choose from when solving the task. It can either choose to convolve the input, or to pool it directly. The final architecture contains multiple of these inception modules stacked one over the other. Even the training is slightly different in GoogleNet, as most of the topmost layers have their own output layer. This nuance helps the model converge faster, as there is a joint training as well as parallel training for the layers itself.

4. ResNet—ResNet is one of the monster architectures which truly define how deep a deep learning architecture can be. Residual Networks (ResNet in short) consists of multiple subsequent residual modules, which are the basic building block of ResNet architecture. ResNet uses of standard SGD instead of a fancy adaptive learning technique. This is done along with a reasonable initialization function which keeps the training intact; Changes in preprocessing the input, where the input is first divided into patches and then feeded into the network. The main advantage of ResNet is that hundreds, even thousands of these residual layers can be used to create a network and then trained. This is a bit different from usual sequential networks, where you see that there is reduced performance upgrades as you increase the number of layers.

5. ResNeXt—ResNeXt is said to be the current state-of-the-art technique for object recognition. It builds upon the concepts of inception and resnet to bring about a new and improved architecture.

6. RCNN (Region Based CNN)—Region Based CNN architecture is said to be the most influential of all the deep learning architectures that have been applied to object detection problem. To solve detection problem, what RCNN does is to attempt to draw a bounding box over all the objects present in the image, and then recognize what object is in the image.

7. YOLO (You Only Look Once)—YOLO is a real time system built on deep learning for solving image detection problems. As seen in the below given image, it first divides the image into defined bounding boxes, and then runs a recognition algorithm in parallel for all of these boxes to identify which object class do they belong to. After identifying this classes, it goes on to merging these boxes intelligently to form an optimal bounding box around the objects. All of this is done in parallely, so it can run in real time; processing up to 40 images in a second.

8. SqueezeNet—The squeezeNet architecture is one more powerful architecture which is extremely useful in low bandwidth scenarios like mobile platforms. This architecture has occupies only 4.9 MB of space, on the other hand, inception occupies ~100 MB! This drastic change is brought up by a specialized structure called the fire module which is good for mobile phone.

9. SegNet—SegNet is a deep learning architecture applied to solve image segmentation problem. It consists of sequence of processing layers (encoders) followed by a corresponding set of decoders for a pixelwise classification. Below image summarizes the working of SegNet. One key feature of SegNet is that it retains high frequency details in segmented image as the pooling indices of encoder network is connected to pooling indices of decoder networks. In short, the information transfer is direct instead of convolving them. SegNet is used for dealing with image segmentation problems.

The system can detect neurologic problems, as almost every neurologic condition will be associated in some way with an abnormality of gait, such as an inability to gait, knuckling, lameness, unsteadiness, or development of a protective mode of walking evidencing severe pain.

While the system described above is susceptible to various modifications and alternative constructions, certain illustrated embodiments thereof are shown in the drawings and have been described above in detail. It should be understood, however, that there is no intention to limit the system to the specific form or forms disclosed, but on the contrary, the intention is to cover all modifications, alternative constructions, and equivalents falling within the spirit and scope of the above system.

What is claimed is:

1. A method, comprising:
characterizing a user glucose absorption of a plurality of food products and generating a response curve for each food product for use in estimating glucose level in a user;
continuously capturing vital signs and motion data from a wearable device including one or more non-invasive glucose, vital sign and motion sensors adapted to be coupled to a user;
capturing food consumption of the user;
predicting a predetermined health condition of the user based on the user glucose level based on output from the non-invasive glucose sensor and the response curve, vital signs, and motion data detected by the wearable device;
generating a plan by the wearable device to control user glucose for controlling diet and physical activity with feedback from the vital signs, motion data and glucose level; and
prompting the user with the wearable device to execute the plan with a closed-loop feedback based on sensor data.

2. The method of claim 1, comprising determining an effect of a predetermined food item on glucose.

3. The method of claim 2, comprising determining an effect of a second food item on glucose when taken with the predetermined food item.

4. The method of claim 1, comprising prompting the user with the mobile device to perform a physical activity within a selected time period after a meal to keep glucose level in a predetermined range.

5. The method of claim 1, comprising providing customized coaching with the mobile device to the user to achieve the plan.

6. The method of claim 1, comprising adjusting via the mobile device a timing or intensity of a selected physical activity to maintain a glucose target.

7. The method of claim 1, comprising estimating a glucose level using bio-impedance sensors.

8. The method of claim 1, comprising measuring a user weight with a weight sensor and determining a weight loss program.

9. The method of claim 1, comprising measuring user activity or exercise with the mobile device and determining a weight loss program.

10. The method of claim 1, comprising determining via the mobile device user smoking or drug dependency and weaning the user from smoking or drug through a series of behavioral changes including exercise.

11. The method of claim 1, wherein the predetermined health condition comprises high blood pressure.

12. The method of claim 1, comprising cuff-less blood pressure sensing in a closed-loop feedback.

13. The method of claim 1, comprising upon detecting a blood pressure above a threshold, immediately reducing blood pressure with a diuretics, an angiotensin-converting enzyme (ACE) inhibitor, an angiotensin II receptor blocker (ARB), calcium channel blocker, alpha blocker, alpha-beta blocker, beta blocker, renin inhibitor, aldosterone antagonist, garlic, music therapy, biofeedback, deep breathing, or exercise.

14. The method of claim 1, comprising providing a biofeedback sensor to reduce blood pressure in real time.

15. The method of claim 1, comprising training a neural network with user data from the mobile device to model user states.

16. The method of claim 15, comprising performing with a remote computer distributed edge learning with differential privacy.

17. The method of claim 1, comprising social networking with people having selected user health characteristics.

18. The method of claim 1, wherein the coaching provides exercise feedback.

19. The method of claim 1, comprising using a wrist device with a deep penetrating optical beam to detect glucose from veins under a skin.

20. A method, comprising: characterizing a user glucose absorption of a plurality of food products and generating a response curve for each food product for use in estimating glucose level in a user
- continuously capturing vital signs and motion data from a wearable device including one or more blood pressure, vital sign and motion sensors adapted to be coupled to a user;
- performing non-invasive sensing using the wearable device to detect blood pressure level;
- capturing food consumption of the user with a mobile device;
- predicting a predetermined health condition of the user based on the vital signs and motion data collected by the wearable device;
- generating a plan with the mobile device to delay an onset of medication requirement by addressing the predetermined health condition of blood pressure and treating blood pressure in real-time by controlling diet and physical activity with feedback from the vital signs, motion data and blood pressure level; and
- prompting the user with the mobile device to execute the plan with a closed-loop feedback based on sensor data.

* * * * *